(12) United States Patent
Harley et al.

(10) Patent No.: US 10,324,068 B2
(45) Date of Patent: Jun. 18, 2019

(54) TEMPERATURE COMPENSATION IN WAVE-BASED DAMAGE DETECTION SYSTEMS

(71) Applicant: Carnegie Mellon University, Pittsburgh, PA (US)

(72) Inventors: Joel B. Harley, Pittsburgh, PA (US); Jose M. F. Moura, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 1038 days.

(21) Appl. No.: 13/945,766

(22) Filed: Jul. 18, 2013

(65) Prior Publication Data

US 2014/0025316 A1    Jan. 23, 2014

Related U.S. Application Data

(60) Provisional application No. 61/741,434, filed on Jul. 19, 2012.

(51) Int. Cl.
G01N 29/44    (2006.01)
G01N 29/24    (2006.01)
G01N 29/46    (2006.01)

(52) U.S. Cl.
CPC .......... *G01N 29/44* (2013.01); *G01N 29/245* (2013.01); *G01N 29/4463* (2013.01); *G01N 29/46* (2013.01); *G01N 2291/0258* (2013.01); *G01N 2291/0425* (2013.01)

(58) Field of Classification Search
None
See application file for complete search history.

(56) References Cited

U.S. PATENT DOCUMENTS

| | | | | |
|---|---|---|---|---|
| 2,922,146 A | * | 1/1960 | Smith | G01B 5/0002 336/119 |
| 4,464,725 A | * | 8/1984 | Briefer | G01G 7/06 177/25.13 |
| 4,757,263 A | * | 7/1988 | Cummings, III | G01R 15/14 324/126 |

(Continued)

OTHER PUBLICATIONS

*Electric Power Group v. Alstom* (See Attached Case).*

(Continued)

*Primary Examiner* — Janet L Suglo
*Assistant Examiner* — Leonard S Liang
(74) *Attorney, Agent, or Firm* — Fish & Richardson P.C.

(57) ABSTRACT

A method performed by a processing device, the method comprising: obtaining first waveform data indicative of traversal of a first signal through a structure at a first time; applying a scale transform to the first waveform data and the second waveform data; computing, by the processing device and based on applying the scale transform, a scale-cross correlation function that promotes identification of scaling behavior between the first waveform data and the second waveform data; performing one or more of: computing, by the processing device and based on the scale-cross correlation function, a scale factor for the first waveform data and the second waveform data; and computing, by the processing device and based on the scale-cross correlation function, a scale invariant correlation coefficient between the first waveform data and the second waveform data.

19 Claims, 13 Drawing Sheets

(56) References Cited

U.S. PATENT DOCUMENTS

| | | | | |
|---|---|---|---|---|
| 5,229,612 | A * | 7/1993 | Pompei | G01J 5/14 250/338.1 |
| 5,319,202 | A * | 6/1994 | Pompei | G01J 5/14 250/252.1 |
| 5,735,605 | A * | 4/1998 | Blalock | G01K 7/14 374/179 |
| 5,826,982 | A * | 10/1998 | Schieferdecker | H05B 6/68 219/494 |
| 6,115,441 | A * | 9/2000 | Douglass | G01K 1/028 374/163 |
| 6,314,380 | B1 * | 11/2001 | Seip | B06B 1/0215 280/735 |
| 6,639,506 | B1 * | 10/2003 | Landis | G01F 1/684 338/25 |
| 6,738,722 | B2 * | 5/2004 | Polla | G01D 3/022 702/104 |
| 7,171,269 | B1 * | 1/2007 | Addison | A61B 5/0452 128/901 |
| 7,805,262 | B2 * | 9/2010 | Slater | G01K 13/00 702/61 |
| 7,826,991 | B2 * | 11/2010 | Schumacher | G01K 3/06 702/98 |
| 2006/0064012 | A1 * | 3/2006 | Waag | G01S 7/52049 600/437 |
| 2007/0100596 | A1 * | 5/2007 | Hollis | G06F 17/5036 703/14 |
| 2008/0133982 | A1 * | 6/2008 | Rawlins | H03F 1/0211 714/699 |
| 2010/0165521 | A1 * | 7/2010 | Changali | H02H 1/0015 361/42 |
| 2010/0331715 | A1 * | 12/2010 | Addison | A61B 5/02028 600/529 |
| 2011/0313777 | A1 * | 12/2011 | Baeckstroem | G10L 25/90 704/500 |
| 2012/0076435 | A1 * | 3/2012 | Sharma | G06T 1/0064 382/277 |

OTHER PUBLICATIONS

Harley et al; Scale Transform Signal Processing for Optimal Ultrasonic Temperature Compensation; IEEE Transactions on Ultrasonics Ferroelectrics and Frequency Control—Oct. 2012 (Year: 2012).*

Roy et al; "A novel physics-based temperature compensation model for structural health monitoring using ultrasonic guided waves"; Structural Health Monitoring, 2014, vol. 13(3) 321-342 (Year: 2014).*

P. Cawley, "Practical long range guided wave inspection—managing complexity," *Review of Progress in Quantitative Nondestructive Evaluation*, vol. 22, No. 657, pp. 22-40, 2003.

P. Wilcox, M. Lowe, and P. Cawley, "Mode and transducer selection for long range Lamb wave inspection," *J. Intel. Mat. Syst. Str.*, vol. 12, No. 8, pp. 553-565, Aug. 2001.

D. N. Alleyne and P. Cawley, "The interaction of Lamb waves with defects." *IEEE Trans. Ultrason., Ferroelectr., Freq. Control*, vol. 39, No. 3, pp. 381-97, Jan. 1992.

J. Michaels and T. Michaels, "Detection of structural damage from the local temporal coherence of diffuse ultrasonic signals," *IEEE Trans. Ultrason., Ferroelectr.; Freq. Control*, vol. 52, No. 10, pp. 1769-1782, Oct. 2005.

G. Konstantinidis, P. D. Wilcox, and B. W. Drinkwater, "An investigation into the temperature stability of a guided wave structural health monitoring system using permanently attached sensors," *IEEE Sensors J.*, vol. 7, No. 5, pp. 905-912, May 2007.

K. Salmna and C. K. Ling, "The effect of stress on the temperature dependence of ultrasonic velocity," *J. Appl. Phys.*, vol. 51, No. 3, pp. 1505-1509, Mar. 1980.

A. Raghavan and C. E. Cesnik, "Effects of elevated temperature on guided-wave structural health monitoring," *J. Intel. Mat. Syst. Str.*, vol. 19, No. 12, pp. 1383-1398, May 2008.

Y. Lu and J. E. Michaels, "A methodology for structural health monitoring with diffuse ultrasonic waves in the presence of temperature variations," *Ultrasonics*, vol. 43, No. 9, pp. 717-31, Oct. 2005.

A. J. Croxford, P. D. Wilcox, Y. Lu, J. Michaels, and B. W. Drinkwater, "Quantification of environmental compensation strategies for guided wave structural health monitoring," in *Proc. SPIE*, 2008, pp. 69 350H. 1-69 350H.11.

R. Weaver and O. Lobkis, "Temperature dependence of diffuse field phase," *Ultrasonics*, vol. 38, No. 1-8, pp. 491-494, Mar. 2000.

T. Clarke, F. Simonetti, and P. Cawley, "Guided wave health monitoring of complex structures by sparse array systems: Influence of temperature changes on perform,race," *J. Sound Vib.*, vol. 329, No. 12, pp. 2306-2322, Jun. 2010.

A. J. Croxford, J. Moll, P. D. Wilcox, and J. E. Michaels, "Efficient temperature compensation strategies for guided wave structural health monitoring," *Ultrasonics*, vol. 50, No. 4-5, pp. 517-528, Apr. 2010.

Y. Lu, J. E. Michaels, and S. Member, "Feature extraction and sensor fusion for ultrasonic structural health monitoring under changing environmental conditions," *IEEE Sensors J.*, vol. 9, No. 11, pp. 1462-1471, Sep. 2009.

J. Bertrand, P. Bertrand, and J. Ovarlez, *Transforms and Applications Handbook*, 3rd ed. Boca Raton: CRC Press, 2010, ch. 12, pp. 12-1-12-37.

D. Casasent and D. Psaltis, "Scale invariant optical correlation using Mellin transforms," *Opt. Commun.*. vol. 17, No. 1, pp. 59-63, Apr. 1976.

P. L. Butzer and S. Jansche, "A direct approach to the Mellin transform," *J. Fourier Anal. Appl.*, vol. 3, No. 4, pp. 325-376, Jul. 1997.

B. Epstein, "Some applications of the Mellin transform in statistics," *Ann. Math. Stat.*, vol. 19, No. 3, pp. 370-379, Sep. 1948.

Z. A. Lomnicki, "On the distribution of products of random variables," *J. R. Stat. Soc. Ser. B Stat. Methodol.*, vol. 29, No. 3, pp. 513-524, 1967.

K. Subrahmaniam, "On some applications ofMellin transforms to statistics : Dependent random variables," *SIAM J. Appl. Math.*, vol. 19, No. 4, pp. 658-662, Dec. 1970.

P. Flajolet, "Mellin transforms and asymptotics: Harmonic sums," *Theor. Comput. Sci.*, vol. 144, No. 1-2, pp. 3-58, Jun. 1995.

A. De Sena and D. Rocchesso, "A Fast Mellin and Scale Transform," *EURASIP J. Adv. Sig. Pr.*, vol. 2007. No. 1, pp. 1-10, Jan. 2007.

P. E. Zwicke and 1. Kiss, "A new implementation of the Mellin transform and its application to radar classification of ships," *IEEE Trans. Pattern Anal. Math. Intell.*, vol. PAM1-5, llo. 2, pp. 191-199. Mar. 1983.

T. Irino, "Segregating information about the size and shape of the vocal tract using a time-domain auditory model: The stabilised wavelet-Mellin transform," *Speech Commun.*, vol. 36, No. 3-4, pp. 181-203, Mar. 2002.

R. A. Altes and L. Jolla, "The Fourier-Mellin transform and mammalian hearing," *J. Acoust. Soc. Am.*, vol. 63, No. 1, pp. 174-183, Jan. 1978.

S. Derrode and F. Ghorbel, "Robust and efficient Fourier-Mellin transform approximations for gray-level image reconstruction and complete invariant description," *Comput. Vis. Image Und.*, vol. 83, No. 1, pp. 57-78, Jul. 2001.

J. Yang, T. Sarkar, and P. Antonik, "Applying the Fourier-modified Mellin transform (FMMT) to Doppler-distorted waveforms," *Digit. Signal Process.*, vol. 17, No. 6, pp. 1030-1039, Nov. 2007.

Y. Sheng and H. H. Arsenault, "Experiments on pattern recognition using invariant Fourier-Mellin descriptors," *J. Opt. Soc. Am.*, vol. 3, No. 6, pp. 771-776, Jun. 1986.

C. Y. Lin, M. Wu, J. A. Bloom, I. J. Cox, M. L. Miller, and Y. M. Lui, "Rotation, scale, and translation resilient watermarking for images," *IEEE Trans. Image Process.*, vol. 10, No. 5, pp. 767-782, Jan. 2001.

Q. Chen, M. Defrise, and F. Deconinck, "Symmetric phase-only matched filtering of Fourier-Mellin transforms for image registration and recognition," *IEEE Trans. Pattern Anal. Mach. Intell.*, vol. 16, No. 12, pp. 1156-1168, Dec. 1994.

(56) References Cited

OTHER PUBLICATIONS

B. S. Reddy and B. N. Chatterji, "An FFT-based technique for translation, rotation, and scale-invariant image registration," *IEEE Trans. Image Process.*, vol. 5, No. 8, pp. 1266-1271, Jan. 1996.

R. Cassinis, "Unsupervised matching of visual landmarks for robotic homing using Fourier-Mellin transform," *Robot. Auton. Syst.*, vol. 40, No. 2-3, pp. 131-138, Aug. 2002.

J. Zhang, Z. Ou, and H. Wei, "Fingerprint matching using phase-only correlation and Fourier-Mellin transforms," in *Sixth International Conference on Intelligent Systems Design and Applications*, Jinan, Oct. 2006, pp. 379-383.

F. Ghorbel, "A complete invariant description for gray-level images by the harmonic analysis approach," *Pattern Recogn. Lett.*, vol. 15, No. 10, pp. 1043-1051, Oct. 1994.

L. Cohen, "The scale representation," *IEEE Trans. Signal Process.*, vol. 41, No. 12, pp. 3275-3292, Dec. 1993.

Y. Jiang and A. Papandreou-Suppappola, "Discrete time-scale characterization of wideband time-varying systems," *IEEE Trans. Signal Process.*, vol. 54, No. 4, pp. 1364-1375, Apr. 2006.

D. M. Ruth and J. E. Gilbert, "The Mellin transform in signal analysis," Texas University at Austin Applied Research Labs, Austin, Tech. Rep., 1994.

J. B. Miller, "Hilbert spaces of generalized functions extending L2, (I)," *J. Austral. Math. Soc.*, vol. 1, No. 3, pp. 281-298, Apr. 1960.

A. De Sena, "A computational framework for sound analysis with the Mellin and scale transform," PhD, Universit'a di Verona, 2008.

A. V. Oppenheim, R. W. Schafer, and J. R. Buck, *Discrete-time Signal Processing*, 2nd ed., ser. Prentice Hall Signal Processing Series. Upper Saddle River: Prentice Hall, 1999.

M. Unser, "Splines: a perfect fit for signal and image processing," *IEEE Signal Process. Mag.*, vol. 16, No. 6, pp. 22-38, Nov. 1999.

W. H. Press, S. A. Teukolsky, W. T. Vetterling, and B. P. Flannery, *Numerical Recipes*, 3rd ed. New Yorki Cambridge University Press, 2007.

W. J. Williams, "Scale and translation invariant methods for enhanced time-frequency pattern recognition," *Multidim. Syst. Sign. Process.*, vol. 473. No. 4. pp. 465-473. Oct. 1998.

G. Robbins and T. Huang, "Inverse filtering for linear shift-variant imaging systems," *Proc. IEEE.* vol. 60. No. 7, pp. 862-872, Jul. 1972.

H. Sundaram, S. Joshi, and R. Bhatt, "Scale periodicity and its sampling theorem," *IEEE Trans. Signal Process.*, vol. 45, No. 7, pp. 1862-1865, Jul. 1997.

R. Wolke and H. Schwetlick, "Iteratively Reweighted Least Squares: Algorithms, Convergence Analysis, and Numerical Comparisons," *SIAMJ. Sci. Stat. Comput.*, vol. 9, No. 5, p. 907, Sep. 1988.

\* cited by examiner

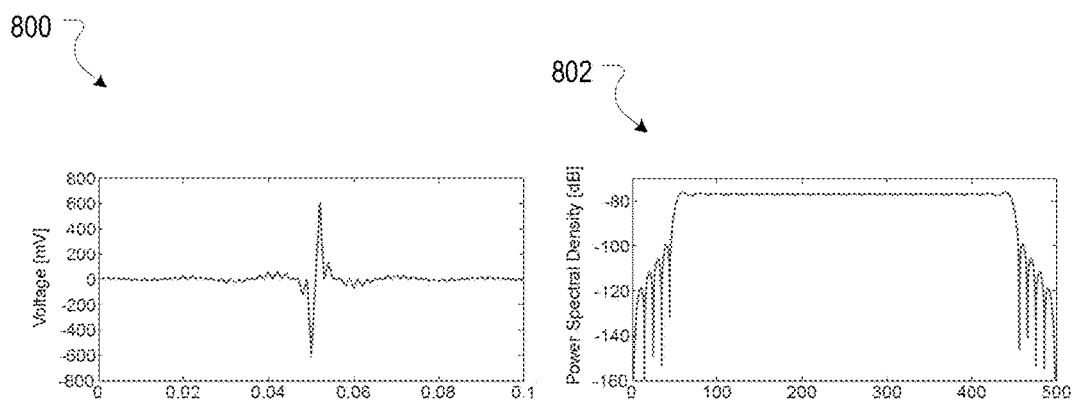
FIG. 8A Excitation time domain signal    FIG. 8B Excitation power spectral density

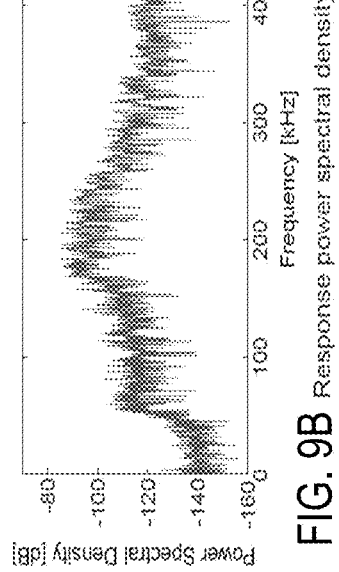
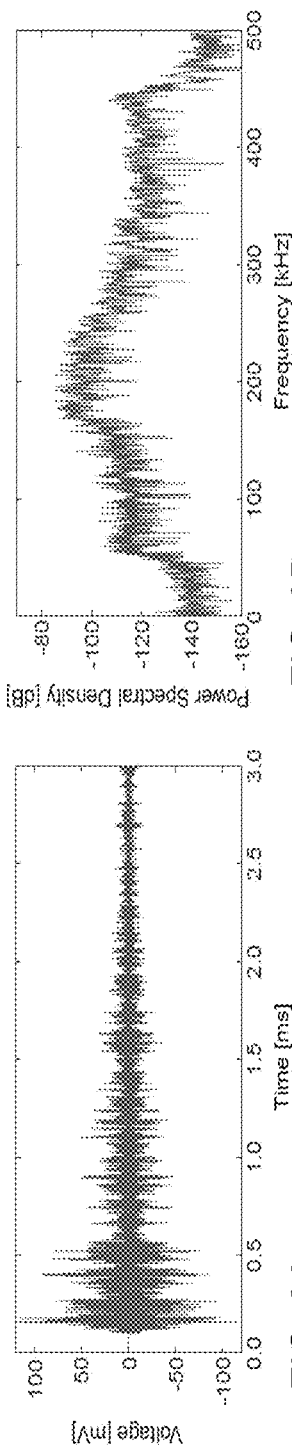
FIG. 9A Response time domain signal
FIG. 9B Response power spectral density

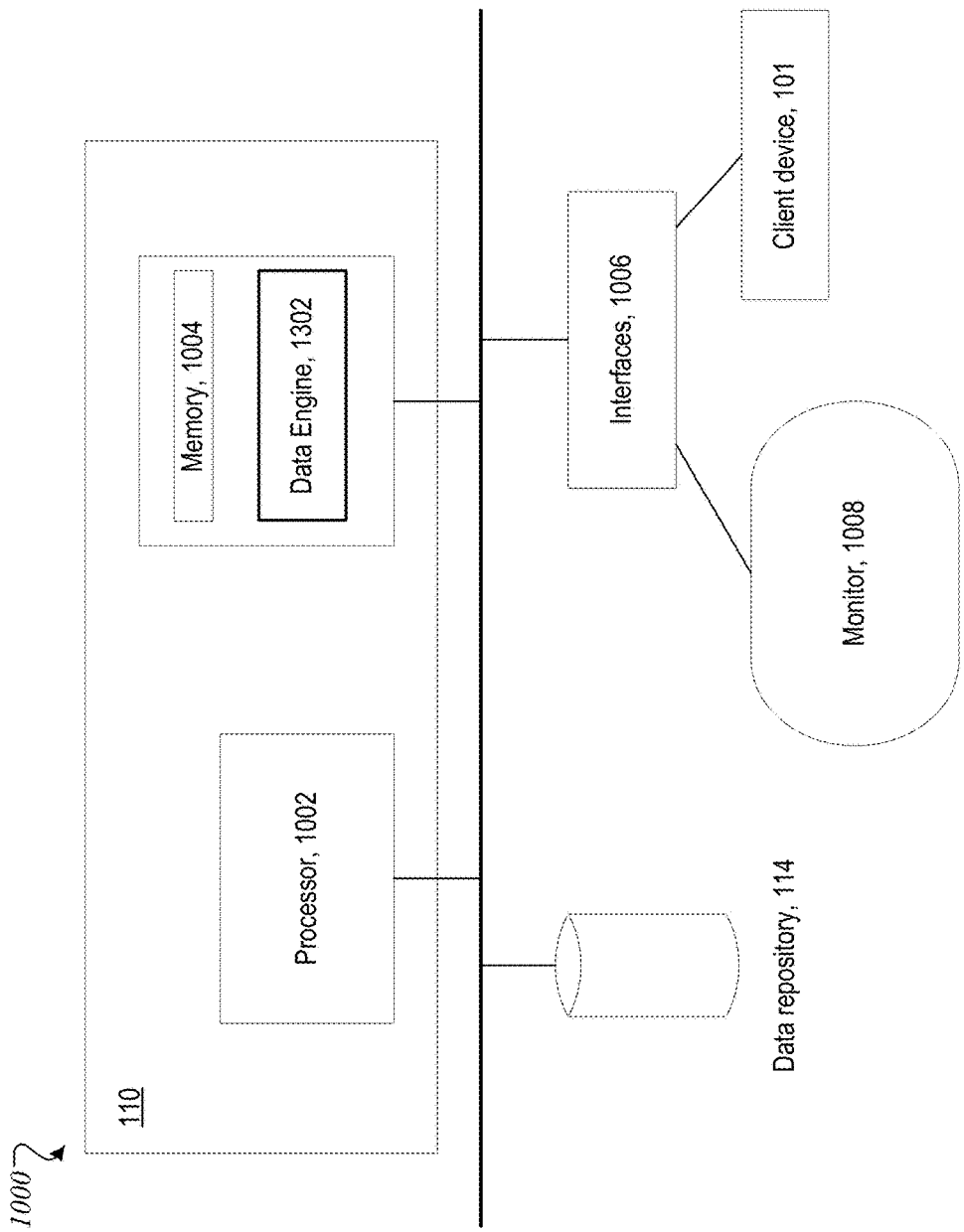

TEMPERATURE COMPENSATION IN WAVE-BASED DAMAGE DETECTION SYSTEMS

CLAIM OF PRIORITY

This application claims priority under 35 U.S.C. § 119(e) to provisional U.S. Patent Application 61/741,434, filed on Jul. 19, 2012, the entire contents of which is hereby incorporated by reference.

BACKGROUND

Structural health monitoring systems (SHM) and other damage detection systems use guided wave inspection methods for testing large structures. Guided ultrasonic waves are popular because they travel through the thickness of the structure over long distances with little attenuation. This allows sensors to interrogate large areas all at once. However, guided waves are inherently multi-modal and dispersive in their propagation. Furthermore, structures' boundaries generate reflections and exchange energy between wave modes. These effects make the interpretation of measured data difficult and necessitate the use of baseline measurements with no damage present.

Under ideal conditions, SHM techniques easily detect damage as a change in the propagation medium by performing a subtraction or time domain correlation with a baseline signal. The baseline reduces complexity by removing effects from static sources, such as reflecting boundaries. Unfortunately, when the environmental conditions change, these methods are unable to distinguish damage from benign effects.

Temperature Compensation

One of the most prominent environmental effects to distort signals is temperature fluctuation. Temperature has been shown to modify the velocity of the guided wave modes, which stretches or scales the measured time domain signal. Given an ultrasonic signal measurement x(t), a change in temperature $T\{\cdot\}$ can be modeled as a uniform scale $$T\{x(t)\} = x(\alpha t), \quad (1)$$

where $\alpha$ is an unknown scaling factor. This effect can be attributed to temperature's influence on the Young's modulus of the material.

However, this model is an approximation. In the presence of multi-modal and dispersive propagation, temperature's effects do not perfectly dilate or compress the signal. Even so, the effectiveness of this approximate model has been experimentally demonstrated in references. This implies that, by computing a scale-invariant measure of similarity between the baseline signal and measured data, one can compensate for temperature's effects on the ultrasonic signals. Two prior art techniques have been proposed for ultrasonic temperature compensation by computing a scale-invariant statistic: (a) optimal signal stretch, and (b) local peak coherence.

Optimal Signal Stretch

Optimal signal stretch (OSS) is prior art technique for ultrasonic temperature compensation that uses an exhaustive search optimization strategy for finding the scale factor $\alpha$ which minimizes the mean squared error between baseline and measured data. OSS employs a finite library of K stretched baselines $\{s(\alpha_1 t), s(\alpha_2 t), \ldots, s(\alpha_K t)\}$ and computes the mean squared error between the observed signal and each element in the library. The scale factor which minimizes the mean squared error is then declared to be the optimal choice over the given set. As $K \to \infty$, OSS computes the optimal scale factor, over all possible scale factors, that minimizes the mean squared error.

When the baseline and observed data are normalized to have zero means and equal $L^2$ norms, minimizing the mean squared error is equivalent to maximizing the sample Pearson product-moment correlation coefficient, or correlation coefficient for short. In the use of OSS, data is normalized so that changes in the signal mean or amplitude, which generally do not correspond with damage, do not bias the results. With normalizing the data, the optimal scale factor $\alpha$ chosen by OSS is defined by $$\alpha = \underset{k}{\mathrm{argmax}} \int_0^\infty \frac{(x(t) - \mu_x)(s(\alpha_k t) - \mu_{s,k})}{\sigma_x(\sigma_s / \sqrt{\alpha_k})} dt, \; 1 < k < K, \quad (2)$$

where $\beta$ and $\sigma$ represent the mean and $L^2$ norm of each signal, $$\mu_x = \lim_{T \to \infty} \frac{1}{T} \int_0^T x(t) dt \quad (3)$$

$$\sigma_x = \sqrt{\int_0^\infty |x(t) - \mu_x|^2 dt}.$$

The correlation coefficient between the optimally scaled baseline $s(\alpha\, t)$ and observed data $x(t)$ can then be expressed as $$\phi_{xs} = \underset{k}{\max} \int_0^\infty \frac{(x(t) - \mu_x)(s(\alpha_k t) - \mu_{s,k})}{\sigma_x(\sigma_s / \sqrt{\alpha_k})} dt, \; 1 < k < K, \quad (4)$$

where value of $\varphi_{xs}$ has a range $-1 \leq \varphi_{xs} \leq 1$. As $K \to \infty$, $\varphi_{xs}$ becomes scale-invariant. So if $x(t)$ and $s(t)$ are scaled replicas of one another (i.e., $x(t) = s(\alpha\, t)$), then the value of $\varphi_{xs}$ is 1. Conversely, if $x(t) = -s(\alpha\, t)$, then the value of $\varphi_{xs}$ is $-1$. When there is no scale relationship between the two signals, $\varphi_{xs} = 0$. For finite values of K and situations in which $x(t) \approx s(\alpha\, t)$, $\varphi_{xs}$ describes the degree of linear correlation between $x(t)$ and the optimally scaled baseline $s(\alpha\, t)$.

Since OSS is an optimal technique, assuming the uniform scaling model described in (1), system 110 uses it as a baseline for comparing the techniques described herein and other techniques. Although effective, OSS is computationally inefficient. For a discrete signal of N samples and a library of K stretched baselines, the OSS correlation coefficient can be computed using a matrix-vector multiplication. The computationally complexity of this operation, in big-O notational, is $O(K\,N)$. Therefore, for sufficiently large signals and a sufficiently dense library, OSS becomes computationally impractical.

Local Peak Coherence

A second prior art approach to ultrasonic temperature compensation is referred to as the local peak coherence (LPC) technique, which is used to estimate the scale factor from local delay measurements. It has been experimentally shown that diffuse-like signals, cluttered by reflections and multi-path propagation, also exhibit almost perfect signal stretching behavior as temperature varies. Since the diffuse-like condition ensures the measured signal to have a long and continuous duration, the scale factor between the two signals can be estimated from a series of local delay estimates. LPC assumes that, given an observed signal x(t) and uniformly scaled replica x(t)=s($\alpha$ t), the uniform scaling effect can be approximated as a delay in a small region around t=$t_0$, $$x(t)=s(\alpha t)\approx s(t-(1+\alpha)t_0) \text{ as } t\to t_0. \quad (5)$$

To estimate these delays, a small portion of each signal is windowed around time t=$t_0$ and the delay between each windowed signal is computed as the argument that maximizes the standard cross-correlation (coherence) function, $$d_w = \underset{t}{\operatorname{argmax}} \int_0^\infty x_w(\tau)s_w(t+\tau)d\tau, 1 < w < W, \quad (6)$$

where $d_w$ is the delay estimate for window w, $s_w(t)$ and $x_w(t)$ are windowed baseline and observed signals, and W is the number of window positions. As the window moves across each signal, the delay value increases linearly according to the scale factor. The scale parameter is then computed by performing a regression analysis on the estimated delays. Using the computed scale factor, the correlation coefficient between the appropriately scaled baseline and measured data is then computed and used as the scale-invariant statistic.

As compared with OSS, LPC can be computed very quickly. The delay estimates may be computed using the fast Fourier transform (FFT) algorithm. Assuming, $N_w$ is the number of discrete samples in the window and there are W different window positions, computing every delay requires a computational complexity of O(W $N_w$ log($N_w$)). In general, $N_w$ will be small. So overall, the computational efficiency is linearly dependent on W, and at a minimum, the scale factor can be estimated using W=2. However, this efficiency comes at the cost of robustness. The technique approximates uniform scaling as a series of delays, which, as shown in equation (5), is true asymptotically as t→$t_0$. In general, this may not always be a good approximation. Also, any effect that does not uniformly scale the signal may disrupt a portion of a delay estimates and may significantly alter the scale factor estimate. For this reason, LPC is not robust and may be adversely affected by many effects, including the introduction of damage.

Therefore there is still a need for methods for compensation for temperature variations in ultrasonic inspection systems that provide high quality results and do so rapidly.

SUMMARY

In one aspect of the present disclosure, a method performed by one or more processing devices comprises obtaining first waveform data indicative of traversal of a first signal through a structure at a first time, wherein a first ambient temperature is associated with the structure at the first time; obtaining second waveform data indicative of traversal of a second signal through the structure at a second time, wherein a second ambient temperature is associated with the structure at the second time, the first ambient temperature differs from the second ambient temperature, and a difference between the first ambient temperature and the second ambient temperature causes a distortion of the second signal, relative to the first signal, as the second signal traverses through the structure; applying a scale transform to the first waveform data and the second waveform data; computing, by the processing device and based on applying the scale transform, a scale-cross correlation function that promotes identification of scaling behavior between the first waveform data and the second waveform data; performing one or more of: computing, by the processing device and based on the scale-cross correlation function, a scale factor for the first waveform data and the second waveform data, with the scale factor being indicative of an amount of variation between the first ambient temperature and the second ambient temperature; and computing, by the processing device and based on the scale-cross correlation function, a scale invariant correlation coefficient between the first waveform data and the second waveform data, with the scale invariant correlation coefficient comprising a compensation statistic for compensating for the distortion of the second signal, relative to the first signal, that results from variation in the first ambient temperature and the second ambient temperature.

Implementations of the disclosure can include one or more of the following features. In some implementations, the method includes detecting, based on the scale factor and the scale invariant correlation coefficient, one or more areas of structural change in the structure. In other implementations, the structural change comprises a degradation of the structure. In still other implementations, the scale invariant correlation coefficient is indicative of a measure of similarity between the first waveform data and the second waveform data.

In some implementations, the scale factor comprises a value that is used as a multiplier in scaling the first waveform data to correspond to the second waveform data. In still other implementations, the processing device is included in a wave-based damage detection system. In yet other implementations, the structure comprises a concrete structure. In still other implementations, the scale-cross correlation function is computed in accordance with: x(t)$\diamond$ $s_\alpha$(t)=$s^{-1}${$\overline{s\{x(t)\}}s\{s(t)\}$}, wherein $\diamond$ represents a scale cross-correlation operation; wherein the overbar represents a complex conjugation operation; wherein x(t) is the first waveform data; wherein s(t) is the second waveform data; wherein $\alpha$ includes a scaling factor on s(t); wherein s{x(t)} is the scale domain of x(t); wherein s{s(t)} is the scale domain of s(t); and wherein $S^{-1}${•} represents an inverse scale transform.

In yet other implementations, computing the scale-cross correlation function comprises: computing a product of a scale domain of the first waveform data and a scale domain of the second waveform data. In still other implementations, computing the scale-cross correlation function comprises: resampling the first waveform data; resampling the second waveform data; applying an amplification factor to the resampled first and second waveform data; and cross-correlating the amplified, resampled first and second waveform data. In still other implementations, computing the scale-invariant correlation coefficient comprises: determining an increased value of the scale cross-correlation function in a stretch domain factor, relative to other values of the scale cross-correlation function in the stretch domain factor.

In some implementations, one or more of the first signal and the second signal is an ultrasonic wave signal. In still other implementations, the structure comprises one or more of a pipe structure, a heating structure, one or more pipe structures in an oil refinery, one or more pipe structures in a chemical refinery, one or more pipe structures in a gas refinery, one or more natural fuse pipelines, one or more oil pipelines, one or more heating pipe structures, one or more cooling pipe structures, one or more pipe structures in a nuclear power plant, one or more pressure vessels, one or more concrete structures of a bridge, one or more concrete structures of civil infrastructure, one or more portion of an airplace, one or more portions of an aerospace vehicle, one or more portions of a submarine, and one or more metallic structures. In still other implementations, the method includes identifying a maximization of the scale-cross correlation function in the stretch factor domain; wherein computing the scale factor comprises: computing, by the processing device and based on the maximization of the scale-cross correlation function in the stretch factor domain, the scale factor for the first waveform data and the second waveform data; and wherein computing the scale invariant correlation coefficient comprises: computing, by the processing device and based on the maximization of the scale-cross correlation function in the stretch factor domain, the scale invariant correlation coefficient between the first waveform data and the second waveform data.

In still other implementations, the method includes identifying a maximization of the scale-cross correlation function in the scale transform domain; wherein computing the scale factor comprises: computing, by the processing device and based on the maximization of the scale-cross correlation function in the scale transform domain, the scale factor for the first waveform data and the second waveform data; and wherein computing the scale invariant correlation coefficient comprises: computing, by the processing device and based on the maximization of the scale-cross correlation function in the scale transform domain, the scale invariant correlation coefficient between the first waveform data and the second waveform data.

In still another aspect of the disclosure, one or more machine-readable media are configured to store instructions that are executable by a server to perform operations including obtaining first waveform data indicative of traversal of a first signal through a structure at a first time, wherein a first ambient temperature is associated with the structure at the first time; obtaining second waveform data indicative of traversal of a second signal through the structure at a second time, wherein a second ambient temperature is associated with the structure at the second time, the first ambient temperature differs from the second ambient temperature, and a difference between the first ambient temperature and the second ambient temperature causes a distortion of the second signal, relative to the first signal, as the second signal traverses through the structure; applying a scale transform to the first waveform data and the second waveform data; computing, by the processing device and based on applying the scale transform, a scale-cross correlation function that promotes identification of scaling behavior between the first waveform data and the second waveform data; performing one or more of: computing, by the processing device and based on the scale-cross correlation function, a scale factor for the first waveform data and the second waveform data, with the scale factor being indicative of an amount of variation between the first ambient temperature and the second ambient temperature; and computing, by the processing device and based on the scale-cross correlation function, a scale invariant correlation coefficient between the first waveform data and the second waveform data, with the scale invariant correlation coefficient comprising a compensation statistic for compensating for the distortion of the second signal, relative to the first signal, that results from variation in the first ambient temperature and the second ambient temperature. Implementations of this aspect of the present disclosure can include one or more of the foregoing features.

In still another aspect of the disclosure, an electronic system includes a server; and one or more machine-readable media configured to store instructions that are executable by the server to perform operations including: obtaining first waveform data indicative of traversal of a first signal through a structure at a first time, wherein a first ambient temperature is associated with the structure at the first time; obtaining second waveform data indicative of traversal of a second signal through the structure at a second time, wherein a second ambient temperature is associated with the structure at the second time, the first ambient temperature differs from the second ambient temperature, and a difference between the first ambient temperature and the second ambient temperature causes a distortion of the second signal, relative to the first signal, as the second signal traverses through the structure; applying a scale transform to the first waveform data and the second waveform data; computing, by the processing device and based on applying the scale transform, a scale-cross correlation function that promotes identification of scaling behavior between the first waveform data and the second waveform data; performing one or more of: computing, by the processing device and based on the scale-cross correlation function, a scale factor for the first waveform data and the second waveform data, with the scale factor being indicative of an amount of variation between the first ambient temperature and the second ambient temperature; and computing, by the processing device and based on the scale-cross correlation function, a scale invariant correlation coefficient between the first waveform data and the second waveform data, with the scale invariant correlation coefficient comprising a compensation statistic for compensating for the distortion of the second signal, relative to the first signal, that results from variation in the first ambient temperature and the second ambient temperature. Implementations of this aspect of the present disclosure can include one or more of the foregoing features.

All or part of the foregoing can be implemented as a computer program product including instructions that are stored on one or more non-transitory machine-readable storage media, and that are executable on one or more processors. All or part of the foregoing can also be implemented as an apparatus, method, or electronic system that can include one or more processors and memory to store executable instructions to implement the stated operations.

The details of one or more implementations are set forth in the accompanying drawings and the description below. Other features, objects, and advantages will be apparent from the description and drawings, and from the claims.

BRIEF DESCRIPTION OF THE FIGURES

FIGS. 8A-8B show diagrams of a wideband, modulated sinc waveform that captures a frequency spectrum.

FIGS. 9A-9B show graphs indicative of a wideband response of a thin aluminum plate.

FIG. 13 is a block diagram of components in an example environment for generating temperature compensation indicators.

DETAILED DESCRIPTION

A system disclosed herein computes a scale-invariant descriptor based on the Mellin transform, to be used to improve wave-based damage detection systems by compensating for the variation in signals that result from variations in temperature. This compensation statistic is referred to as the scale-invariant correlation coefficient, and the system measures it from the scale cross-correlation function between two signals.

Figure 1:
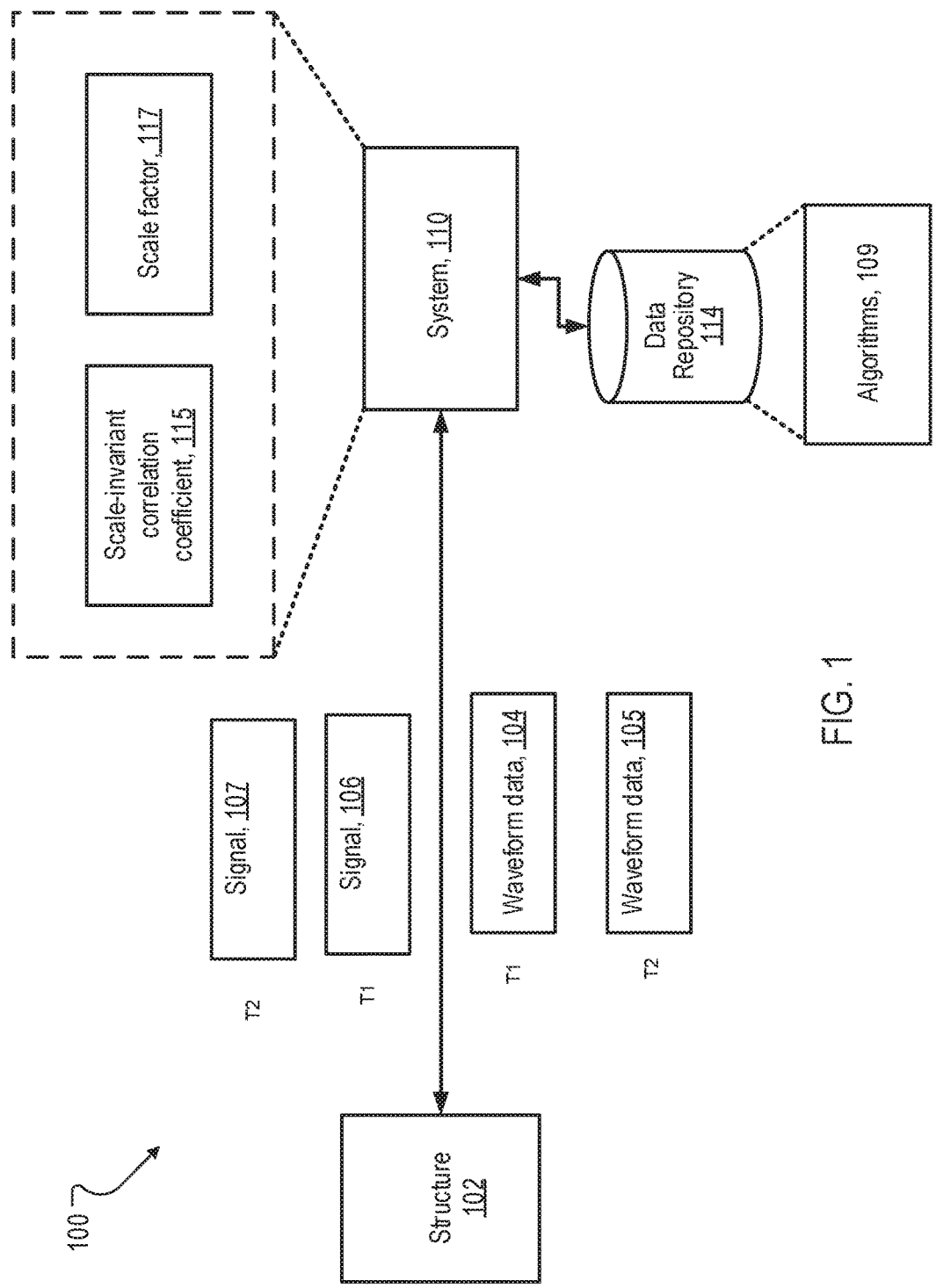
FIG. 1 is block diagram of an example environment for generating temperature compensation indicators.

Referring to FIG. 1, a block diagram is shown of an example environment 100 for generating temperature compensation indicators, e.g., values indicative of an amount to compensate for the variation in signals that result from variations in temperature. There are various types of temperature compensation indictors, including, e.g., a scale invariant coefficient 115, a scale factor 117, and so forth.

Example environment 100 includes structure 102, e.g., a concrete structure, a pipe structure, a heating structure, a refinery, and a nuclear power plant and so forth. Example environment 100 also includes system 110 and data repository 114. In this example, data repository 114 that stores information 109 indicative of various algorithms, including, e.g., algorithms that are represented by and/or in accordance with the equations described herein. In this example, system 110 uses information 109 to compute various temperature compensation indicators.

In the example of FIG. 1, system 110 is configured to emit signals (e.g., ultrasonic wave signals) to structure 102 at various points in time, e.g., a first time (T1) and a second time (T2). Based on the emitted signals, system 110 records waveform data 104, 105 that is indicative of how signals 106, 107, respectively, travel through structure 102 at times T1, T2, respectively. In this example, system 110 detects structural changes (e.g., damage) in structure 102 based on changes in waveform data 104, 105.

In this example, the temperature of structure 102 (e.g., the ambient air surrounding structure 102) fluctuates between time T1 and time T2. These fluctuations cause variations in the waveform data 104, 105. To account for these temperature based variations (which are independent from and different from structural damage), system 110 uses the techniques described herein to compute temperature compensation indicators. By application of the temperature compensation indicators to one or more of waveform data 104, 105, system 110 can identify the variations in waveform data 104, 105 that are caused by temperature fluctuations and compensate for them, e.g., thereby promote detection of variations in waveform data 104, 105 that are caused by structural damage in structure 102. The example environment 100 may include many thousands of client devices and systems.

In this example, one of the algorithms included in information 109 is based on the Mellin transform, which is defined by the integral $$M\{x(t)\} = X(p) = \int_0^\infty x(t)t^{p-1}dt. \quad (7)$$

In some examples, the special case for which $p=-jc$, $$M\{x(t)\} = X(jc) = \int_0^\infty x(t)t^{-jc-1}dt. \quad (8)$$

is also often referred to as the Mellin transform. To avoid confusion, equation (8) is referred to as the Mellin transform and equation (7) as the generalized Mellin transform. Another case of the generalized Mellin transform is known as the scale transform, which system 110 uses to compute the scale-invariant correlation coefficient. Generally, a scale transform includes a modification (e.g., a transform) between two spaces (e.g., a source space and a destination space) where the axis vectors of the source space are longer or shorter than the corresponding axis vectors in the destination space. This causes objects to stretch or shrink along the axes as they are transformed between the two spaces.

In signal processing and computer vision, the Mellin transform has been utilized for its scale-invariant properties. A time-scale operation on the signal x(t) is expressed as a phase change in the Mellin domain, $$M\{x(\alpha t)\} = X(jc)e^{jc\,ln(\alpha)}. \quad (9)$$

The magnitude of the Mellin transform is invariant to changes in the time-scale of a signal. This is analogous to the Fourier magnitude spectrum's shift invariance property.

The generalized Mellin transform is closely related to the Laplace transform. Through algebraic manipulation, the expression for the Mellin transform can be rewritten as $$M\{x(t)\} = X(p) = \int_{-\infty}^\infty x(t)e^{p\ln(t)}d[\ln(t)]. \quad (10)$$

In equation (10), the generalized Mellin transform is equivalent to the Laplace transform, but integrated over logarithmic time. When $p=-j\,c$, the Mellin transform becomes equivalent to the Fourier transform integrated over logarithmic time. This implies that, if an input signal x(t) is exponentially skewed by substituting $t=e^\tau$, the Mellin transform expression becomes $$M\{x(t)\} = X(jc) \quad (11)$$
$$= \int_0^\infty x(e^\tau)e^{-jc\tau}d\tau$$
$$= \mathcal{F}\{x(e^\tau)\},$$

where F {•} represents the Fourier transform. This property is the basis for the fast Mellin transform algorithm.

In engineering, the Mellin transform's scale invariance property has been used in a variety of applications. These applications include the classification of ships from radar signals and the interpretation of speech waveforms. A variant known as the Fourier-Mellin transform is also popular in several engineering fields. The Fourier-Mellin transform is computed from the Mellin transform of the Fourier magnitude spectrum. As a result, the magnitude of the Fourier-Mellin transform achieves invariance to both shifting and scaling. In two dimensions, the Fourier spectrum is also polar transformed to achieve rotation invariance. The Fourier-Mellin transform has been used in applications for the analysis of speech and Doppler waveforms, as well as for pattern recognition and watermark detection in images.

Sometimes, the magnitude of the Mellin transform is analyzed alone to achieve invariance. Unfortunately, this is less than ideal since it requires the removal of phase information, which is necessary for generating complete descriptors of a signal. However, when comparing two signals, the product of the Mellin transformed signals can be used to compute the Mellin cross-correlation function. The maximum of the Mellin cross-correlation is a measure of the scale-invariant similarity between two signals and the location of the maximum can also be used to estimate the scale factor between the signals, as described in further detail below. The Mellin cross-correlation is used in combination with the Fourier-Mellin transform for image registration and pattern recognition applications.

Although the Mellin transform has found widespread use in many applications, there are several difficulties involved with implementing it. First, the Mellin transform of a signal is not guaranteed to exist. Second, in discrete-time, efficient computation of the discrete-time Mellin transform requires data to be exponentially sampled in time. This is often impractical to implement. Therefore, the Mellin transform is usually approximated using the fast Mellin transform algorithm, in which uniformly sampled data is exponentially resampled. However, this non-uniform resampling procedure incurs its own Nyquist sampling restrictions and complicates computation of the associate cross-correlation function.

In this example, the scale cross-correlation function and scale-invariant correlation coefficient, based on the scale-invariant properties of Mellin transform, provide (and/or are used in) ultrasonic temperature compensation. Below, a case of the generalized Mellin transform known as the scale transform is described. The scale transform exists for all finite energy signals. System 110 derives the continuous-time scale cross-correlation and uses it to derive the scale-invariant correlation coefficient and associated scale factor. System 110 also commutates the scale transform and scale cross-correlation in discrete time, and derives the Mellin resampling theorem to address the numerical difficulties with the fast Mellin transform algorithm.

Compared with the temperature compensation methods of the prior art, the techniques for temperature compensation described herein have increased computational speed and robustness (e.g., relative to the computational speed and robustness of the prior art methods). In an example, the continuous-time scale-invariant correlation coefficient described herein is mathematically equivalent to the OSS correlation coefficient as the size of the library $K \to \infty$. This suggests the techniques described herein to be optimal in terms of mean squared error. In an example, the scale-invariant correlation coefficient described herein can be computed very efficiently due to its relationship with the Fourier transform. In this example, the scale-invariant correlation coefficient is as effective as OSS, an optimal method, and more robust than LPC.

In an example, system 110 implements stretch-based, model-driven temperature compensation algorithms based on the scale transform. In the scale transform domain, system 110 manipulates the stretch factor of signals and compute quantities invariant to changes in that stretch factor. System 110 implements three algorithms for temperature compensation based on these scale domain tools: the scale-invariant correlation (SIC) method, the iterative scale transform (IST) method, and the combined SIC/IST method.

The Scale Transform

In an example, system 110 uses the scale transform and scale cross-correlation function for computing the scale factor and the scale-invariant correlation coefficient between two signals. In general, the generalized Mellin transform of equation (7) and the Mellin transform of equation (8) of a signal may not converge. Under appropriate conditions, the generalized Mellin transform of a function $f(t)$ converges within some analytic strip $a < \text{Re}\{p\} < b$, where a and b are real numbers. To promote convergence, system 110 uses the scale transform. The scale transform is a special case of the generalized Mellin transform for which $p = -j\, c + \frac{1}{2}$, $$S\{x(t)\} = X(c) = \int_0^\infty x(t) t^{-jc-1/2} dt. \tag{12}$$

where $S\{\bullet\}$ represents the scale transform. The transform is sometimes normalized by $1/(2\pi)^{1/2}$ to preserve symmetry between it and its inverse. This integral is also sometimes referred to as the Mellin transform or the Mellin transform of square-integrable functions.

The scale transform shares several useful properties with the Fourier transform that are not present in the Mellin transform. For example, the kernel of the inverse scale transform is the complex conjugate of the kernel of the scale transform, as shown in the below equation (13):

$$S^{-1}\{X(c)\} = x(t) \tag{13}$$
$$= \frac{1}{2\pi} \int_{-\infty}^{\infty} X(c) t^{jc-1/2} dc.$$

In equation (13), $S^{-1}\{\bullet\}$ represents the inverse scale transform. The scale transform also satisfies Parseval's theorem. This implies that the $L^2$ norm, or energy, of the signal is conserved between the time and scale domains, in accordance with the below equation (14):

$$\int_0^\infty |x(t)|^2 dt = \int_{-\infty}^{\infty} |X(c)|^2 dc. \tag{14}$$

Therefore, given a finite energy signal, its scale transform and its inverse always exists. Since system 110 is configured to process physical signals that have finite energy, the scale transform may be defined. Parseval's theorem then also implies that the magnitude of the scale transform exhibits invariance to energy-preserving scaling operations, in accordance with the below equation (15):

$$S\{\sqrt{\alpha}x(\alpha t)\} = X(c)e^{jc\,\ln(\alpha)}. \tag{15}$$

As with the Mellin transform, the scale transform is closely related to a logarithmic-time Fourier transform. By performing a change of variables, such that $t = e^\tau$ and $dt = e^\tau d\tau$, the scale transform can be represented in accordance with the below equation (16):

$$S\{x(t)\} = X(c) \tag{16}$$

-continued $$= \int_{-\infty}^{\infty} x(e^\tau) e^{(-jc+1/2)\tau} d\tau$$

$$= \mathcal{F}\{e^{(1/2)\tau} x(e^\tau)\}$$

$$\mathcal{F}\{\tilde{x}(\tau)\}.$$

From this expression, system 110 may also represent the inverse scale transform as indicated in the below equation (17)

$$S^{-1}\{X(c);t\} = e^{-(1/2)ln(t)} F^{-1}\{X(c);\ln(t)\} \quad (17)$$

In an example, system 110 may not compute the inverse scale transform, as performing the substitution of $\tau=\ln(t)$ has several numerical complications. Instead, system 110 may extract the same information using the inverse Fourier transform.

In equation (16), $\tilde{x}(\tau)$ is an energy-preserved, exponentially skewed signal, as demonstrated by performing the same change of variables, where $t=e^\tau$ and $dt=e^\tau d\tau$, to show $$\int_0^\infty |x(t)|^2 dt = \int_0^\infty |e^{(1/2)\tau} x(e^\tau)|^2 dt. \quad (18)$$

Therefore, the scale transform is equivalent to the Fourier transform of a signal that has been exponentially time-skewed with constant energy. When performing the inverse scale transform, system 110 can reverse this process $$\tilde{x}(\tau) = F^{-1}\{X(c)\}, \quad (19)$$

and then perform an energy-preserving logarithmic skew on $\tilde{x}(\tau)$, such that $x(t)=e^{(1/2)ln(t)}\tilde{x}(\ln(t))$, to return the signal to its original domain.

Scale Cross-Correlation Function

As with the Mellin transform, system 110 defines a cross-correlation function between two signals and use it to compute the scale factor and scale-invariant descriptor of similarity between them.

Optimization in the Stretch Factor Domain $\alpha$

The scale cross-correlation function of two signals $x(t)$ and $s(t)$ is defined by the product of their scale domains, as indicated in the below equation (20):

$$x(t) \Diamond s_\alpha(t) = S^{-1}\{\overline{S\{x(t)\}} S\{s(t)\}\}, \quad (20)$$

where $\Diamond$ represents the scale cross-correlation operation and the overbar represents a complex conjugation operation. In the time domain, the scale cross-correlation function is defined in accordance with the below equation (21):

$$\Phi_{xs}(\alpha) = x(t) \Diamond s_\alpha(t) = \int_0^\infty x(t) s(\alpha t) dt \quad \alpha > 0. \quad (21)$$

In equation (21), if $y(t)=x(t) \Diamond s(t)$ is the scale cross-correlation of $x(t)$ and $s(t)$, then $\Phi_{xs}(t)$ is the inner product of every $x(t)$ and $s(\alpha t)$ pair for values of a greater than zero.

In some examples, due to numerical complications, system 110 may not compute the inverse scale transform. To avoid these complications, system 110 further manipulates equation (20) by substituting the inverse scale transform relationship in equation (17) and expressing the scale cross correlation in the ln(a) domain as indicated in the below equation (22):

$$\Phi_{xs}(\alpha)(= e)^{-(1/2) \ln(\alpha)} \mathcal{F}^{-1}\{X*(c)S(c);\ln(\alpha)\} \quad (22)$$

$$= \alpha^{-1/2} \Psi_{xs}(\ln(\alpha)).$$

The function $\psi(\ln(\alpha))$ is another representation for the scale-cross correlation in the $\ln(\alpha)$ domain.

Computation of Scale Invariant Correlation (SIC) Method

For $\Psi_{xs}(\ln(\alpha))$, which may be computable by system 110, the natural logarithm is monotonic and the maximum with respect to $\alpha$ is equivalent to the maximum with respect to $\ln(\alpha)$. Therefore, the maximum corresponds to the same maximum in $\Phi_{xs}(\ln(\alpha))$. Therefore, system 110 computes the optimal stretch factor (e.g., scale factor) as indicated in the below equation (23):

$$\hat{\alpha} = \exp(\operatorname*{argmax}_{\ln(\alpha)} \Psi_{xs}(\ln(\alpha))). \quad (23)$$

System 110 defines a scale-invariant correlation coefficient defined generally by the below equation (24):

$$\phi_{xs} = \max_\alpha \frac{\sqrt{\alpha}}{\sigma_x \sigma_s} \int_0^\infty x*(t) s(\alpha t) dt \quad (24)$$

$$= \max_\alpha \frac{\sqrt{\alpha}}{\sigma_x \sigma_s} \Phi_{xs}(\alpha)$$

$$= \max_{\ln(\alpha)} \frac{1}{\sigma_x \sigma_s} \Psi_{xs}(\ln(\alpha)),$$

where $\varphi_{xs}$ is normalized such that $\varphi_{xs}=1$ when $x(t)$ is a stretched replica of $s(t)$. The scale estimate $\hat{\alpha}$ (e.g., scale factor) specifies how much a signal has scaled or stretch relative to the baseline and the scale-invariant correlation coefficient $\varphi_{xs}$ specifies how similar the two signals are, invariant to scaling or stretching.

Computation of Iterative Scale Transform (IST) Method—Maximization in the Scale Transform Domain c Instead of computing the estimated scale factor directly from the scale-cross correlation function, system 110 computes it through an optimization in the scale transform domain c, e.g., by maximizing the scale-cross correlation function in the scale transforms domain c.

In an example, by applying Parseval's theorem of $$\int_0^\infty x*(t) s(t) dt = \frac{1}{2\pi} \int_{-\infty}^\infty X*(c) S(c) dc$$

and a time stretching property in accordance with $S\{\sqrt{\alpha} x(\alpha t); c\} = X(c) e^{jc \ln(\alpha)}$ to the scale-cross correlation function $\Phi_{xs}(\alpha)$, system 110 expresses an optimal stretch estimate in the scale transform domain (e.g., a scale factor) as indicated in the below equation 25:

$$\hat{\alpha} = \operatorname*{argmax}_\alpha \frac{\sqrt{\alpha}}{\sigma_x \sigma_s} \Phi_{xs}(\alpha) \quad (25)$$

$$\operatorname*{argmax}_\alpha \frac{1}{2\pi \sigma_x \sigma_s} \int_{-\infty}^\infty X*(c) S(c) e^{jc \ln(\alpha)} dc$$

In this example, system 110 modifies the stretch factor α by altering the phase of the scale transform, e.g., by multiplying either X(c) or S(c) by a complex exponential.

The scale-invariant correlation coefficient may then be computed by using from equation (25), in accordance with the below equation (26):

$$\phi_{xs} = \frac{1}{2\pi\sigma_x\sigma_s}\int_{-\infty}^{\infty} X*(c)S(c)e^{jc\,ln(\hat{\alpha})}\,dc. \quad (26)$$

These expressions provide another means of computing the scale factor estimate and scale-invariant correlation coefficient.

Performance of Scale Transform Methods

As discussed in further detail below, system 110 implements SIC technique by computing the scale transform of each signal followed by computing the scale cross-correlation function, from which the scale factor and scale-invariant correlation coefficient is extracted. System 110 implements IST by computing the scale transform of each signal and then uses a standard iterative optimization method to compute the scale factor and scale-invariant correlation coefficient directly from the scale transforms. In an example, the SIC technique may be more computationally efficient, e.g., relative to computation efficiency of the IST technique. In still another example, the IST technique is associated with increased resolution in terms of how accurate the results may be, e.g., relative to the accuracy of the SIC technique.

Scale-Invariant Correlation (SIC) Method

The scale-invariant correlation (SIC) method maximizes $\Phi_{xs}(\ln(\alpha))$ directly in the log-stretch factor domain ln(a) as expressed in equation (23). In this example, by sampling x(t) and s(t) in the time domain and truncating the signal to a length of N samples, the scale transform representations, X(c) and S(c), are represented only by a finite number of values. Using equation (23), system 110 computes $\Phi_{xs}(\ln(\alpha))$ as the inverse Fourier transform of X*(c)S(c). In this example, system 110 evaluates $\Phi_{xs}(\ln(\alpha))$ for a finite, discrete set of stretch factors α.

The resolution of the set of stretch factors is defined by the sampling interval of $\Phi_{xs}(\ln(\alpha))$. Assuming a unitary sampling period, x(t) is defined over the range 1≤t≤N and $x(e^T)$ is defined for 0≤T≤ln(N). In this example, since $x(e^T)$ is of length N ln(N), the interval between each sample is 1/N. In this example, since $\Phi_{xs}(\ln(\alpha))$ is related to $x(e^T)$ and $s(e^T)$ by a Fourier transform followed by an inverse Fourier transform, it also has a sampling interval of 1/N.

This implies that the smallest measurable deviation from α=1 is $$\Delta\alpha = \exp\left(\pm\frac{1}{N}\right). \quad (27)$$

For sufficiently large values of N, system 110 approximates Δα by a first order Taylor series approximate to obtain $$\Delta\alpha \approx 1 \pm \frac{1}{N}. \quad (28)$$

In this example, the resolution of SIC is approximately 1/N. Therefore, SIC is limited in resolution. However, system 110 improves this resolution by combining SIC with an iterative optimization approach.

System 110 calculates the computational complexity of the SIC method. To compute SIC, system 119 exponentially resamples x(t) and s(t), computes Fourier transforms of x(t) and s(t), compute an inverse Fourier transform, and obtains a maximum of the result (and/or an increased value). Maximizing $\Phi_{xs}(\ln(\alpha))$ and exponentially resampling x(t) can both be computed in linear time. In this example, $x(e^T)$ is of length N ln(N) and the computational complexity of computing its Fourier transform, using the fast Fourier transform algorith, is O(N ln(N)log(N ln(N))), or O(N ln(N)log(N)) after simplifying. Since this is the most computationally expensive operation in SIC, the computational complexity of SIC is also O(N ln(N)log(N)).

Iterative Scale Transform (IST) Method

The iterative scale transform (IST) method maximizes the scale cross-correlation function $\Phi_{xs}(\alpha)$ by phase shifting X*(c) or S(c) in the scale transform domain c as shown in equation (60). Solving this optimization problem iteratively in the scale transform domain c allows IST to have increased precision. In an example, the scale cross-correlation is not (globally) convex, but is locally convex around multiple maxima.

To compute the stretch factor estimate $\hat{\alpha}$ using IST, system 110 computes the scale transforms X*(c) and S(c). As with SIC, the complexity of these operation is O(N ln(N)log(N)). System 110 selects an initial guess for α, multiply S(c) (or X*(c)) by $e^{jc\ln(\alpha)}$, and then computes the inner product between X*(c) and $S(c)e^{jc\ln(\alpha)}$. Each of these operations has a linear complexity. This process of choosing an α, applying a phase shift, and computing an inner product is then repeated for different values of α by a vortex optimization algorithm until the inner product converges to a maximum value. The complexity of most convex optimization algorithms, neglecting special cases, is $O(M^2)$ where M is the number of parameters to optimize across. For this application, system 110 optimizes across one variable α, so M=1 and the complexity is constant. Therefore, the complexity of the optimization procedure is O(N ln(N)), for each iteration, where N ln(N) is the number of samples in the scale transform domain.

System 110 also improves the computational speed of IST by taking advantage of the structure of the scale transform. The majority of the energy in a signal is often located early in the scale transform domain. Therefore, system 110 truncates a large portion of the domain with little loss of information. As a result, the cost of the iterative algorith becomes O((ρN ln(N)), where ρ represents the percentage of the scale transform domain retained after truncation.

SIC/IST Combination

As previously discussed, IST is a very precise estimation strategy but only if the result converges to the global maximum. In contrast, SIC requires no assumption of convexity but has a finite resolution. By combining these two methods, system 110 obtains highly precise estimates and guarantees convergence to the global maximum. This is done by using SIC to generate the initial stretch factor estimate $\hat{\alpha}$ for IST. In general, the SIC estimate will lie within the locally convexity region around the global maximum of the scale cross-correlation function $\Phi_{xs}(\alpha)$.

In an example, if N is small enough such that SIC cannot adequately resolve the main lobe of the scale cross-correlation function, then the SIC estimate may not be accurate and IST may not be guaranteed to converge to the globally optimal result. However, for sufficiently large values of N, this is not an issue.

Since IST computes the scale transform representations, X(c) and S(c), the only additional step required when combined with SIC is the computation of the inverse Fourier transform in the below equation (29) and maximization over $\Phi_{xs}(\alpha)$ in equation (23).

$$\hat{\alpha} = \underset{\alpha}{\operatorname{argmax}} \frac{\sqrt{\alpha}}{\sigma_x \sigma_s} e^{-(1/2) \ln(\alpha)} \mathcal{F}^{-1}\{X*(c)S(c); \ln(\alpha)\} \quad (29)$$

$$= \underset{\alpha}{\operatorname{argmax}} \left(\frac{\sqrt{\alpha}}{\sigma_x \sigma_s} \mathcal{F}\right)^{-1} \{X*(c)S(c); \ln(\alpha)\}$$

$$= \underset{\alpha}{\operatorname{argmax}} \frac{\sqrt{\alpha}}{\sigma_x \sigma_s} \Psi_{x,s}(\ln(\alpha)).$$

The computational complexity of these operations is $O(N \ln(N)\log(N))$, the same as initially computing X(c) and S(c). Therefore, these operations do not change the overall computational complexity of IST and the complexity of SIC/IST is equivalent to the computational complexity of IST.

The properties of various temperature compensation techniques are shown in the below Table 1:

TABLE 1

| Methods | | Resolution | Computational Complexity | Iterative Complexity |
| --- | --- | --- | --- | --- |
| Finite Resolution Methods | Search OSS | 1/N | $O(RN^2)$ | — |
|  | SIC | 1/N | $O(N \ln(N)\log(N))$ | — |
| Fine Resolution Methods | Search/ Iterative OSS | — | $O(RN^2)$ | $O(N)$ |
|  | SIC/IST | — | $O(N \ln(N)\log(N))$ | $O(pN \ln(N))$ |

The Discrete-Time Scale Transform

In additional to processing continuous-time signals, system 110 is also configured to process discrete time signals that are sampled. As implied from equations (11) and (18), a discrete-time Mellin transform or discrete-time scale transform (DTST) can be computed by exponentially sampling a continuous-time signal and taking its discrete-time Fourier transform (DTFT). Unfortunately, uniform sampling is usually performed. This presents several challenges in implementing the Mellin or scale transforms.

If the samples are uniformly spaced, then the discrete-time Mellin or scale transforms must be approximated. One option is to replace the continuous-time signals with discrete-time signals and the integrals with summations. However, this provides a poor approximation of the transform. In practice, this "direct" approach has been shown to be less effective than other approximations and is slow, requiring $O(N^2)$ complexity. More often, the Mellin and scale transforms are computed by exponentially resampling the uniformly sampled signal and computing its Fourier transform with the FFT. This is known as the fast Mellin transform (FMT) algorithm.

Compared to the direct Mellin transform approximation, the fast approximation is more accurate and computationally efficient. The exponential resampling operation is implemented by interpolating unknown points on an exponential grid. According to the Nyquist-Shannon sampling theorem, a band-limited signal may be perfectly reconstructed by sinc interpolation. However, performing sinc interpolation on an exponential grid is impractical and computationally expensive. Instead, cubic spline interpolation is commonly used. Cubic spline interpolation provides a close approximation to sinc interpolation and may be computed with O(M) complexity, where M is the number of points on the exponential grid. The DTFT of the resampled signal then is computed using the FFT algorithm, which requires $O(M \log(M))$ complexity.

Mellin Resampling Theorem

Figure 3:
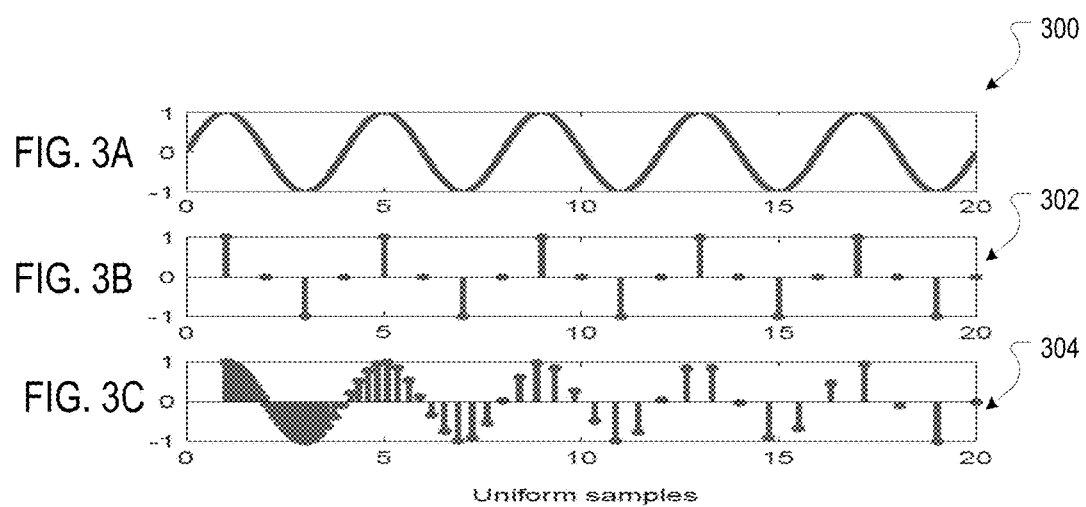
FIGS. 3A-3C show graphs of sampling on a sine wave.

FIGS. 3A-3C illustrate examples of a sinusoid sampled on uniform and an exponential grid. Referring to FIG. 3A, graph 300 illustrates a continuous-time sine wave. Referring to FIG. 3B, graph 302 illustrates a uniformly sampled sine wave. Referring to FIG. 3C, graph 304 illustrates an exponentially sampled sine wave.

In generating an exponentially resampled signal, system 110 uses an exponential grid. To generate the exponential grid, system 110 determines 1) where the first sample in the exponential grid is located in time; and 2) a number of samples to be included in the exponential grid. In this example, system 110 defines the first sample's location and, from that result, derives an exact solution for the necessary number of samples.

In an example, signals may begin at time t=0, which is the scaling origin. In another example, on an exponential grid, t=0 translates to $\tau=\ln(0)=-\infty$. So as the first sample approaches t=0, the sampling interval approaches 0 and the number of necessary samples approaches infinity. To define the location of the first sample, system 110 enforces causality in the exponential-time domain. A causal signal is nonzero for time $\tau \geq 0$. In this example, causality is in exponential time, the signal x(t) will be nonzero for values $\ln(t) \geq 0$ or $t \geq 1$.

When exponential-time causality is assumed, the scale transform becomes $$\mathcal{F}\{e^{(1/2)\tau}x(e^\tau)\} = \int_0^\infty e^{(1/2)\tau}x(e^\tau)e^{-jc}d\tau \quad (30)$$

$$S\{x(t)\} = \int_1^\infty x(t)t^{-jc-1/2}dt.$$

Exponential-time causality implies that the time signal x(t) begins at time t=1. In continuous time, this is not advantageous since it removes data. However, for a uniformly sampled discrete-time signal, this assumption is very practical. In discrete-time, t=nT, where T is the sampling interval. The sampling interval T scales the signal x[nT], which translates to a phase shift in the scale domain, $$S\{x[nT]\}=T^{-1/2}S\{x[n]\}e^{jc\ln(T)}. \quad (31)$$

Therefore, when system 110 computes the DTST, system 110 determines (or accesses information specifying that) the signal has a sampling rate of 1. Under a unitary sampling rate, t=1 occurs when n=1. So in discrete-time, the causality condition allows us to exponentially resample starting from n=1 and neglect the asymptotic conditions around n=0, the scaling origin. This may require us to remove a single sample, assuming the first sample is located on the scaling origin. However, when analyzing the scaling behavior of a signal, the origin contains no information since it is not affected by scaling, $x[\alpha \ 0]=x[0]$, and the scale transform of values at the origin are not well defined. For example, the scale transform of a Dirac impulse $\delta(t)$ is a division by zero $$S\{\delta(t)\} = \int_0^\infty \delta(t) t^{-jc-1/2} dt \qquad (32)$$

$$= \delta(t)(0)^{-jc-1/2}.$$

For these reasons, it is practical for us to assume the first sample is n=1 and the exponential-time domain is causal.

By enforcing causality, the exponentially resampled signal can be computed with a finite number of samples. To properly resample the signal, however, system 110 ensures that no information (or a reduced amount of information) is lost. This condition requires that the minimum sampling rate satisfies the Nyquist sampling criteria, $$\tilde{F}_s \geq 2f_{max}, \qquad (33)$$

where $\tilde{F}_s$ is the minimum sampling rate on the exponential grid and $f_{max}$ is the largest non-zero frequency in the signal. For example, if the uniform signal is critically sampled, where the sampling rate $F_s = 2f_{max}$, then the exponentially resampled signal will require more samples than the uniform signal.

Mellin Resampling Theorem.

In this example, $\tilde{x}[m]$ includes a causal, exponentially resampled signal generated from the uniformly sampled signal x[n], where x[n] is sampled at the Nyquist rate $F_s$, and exists for all integers in the domain 1≤n≤N. Assume $\tilde{x}[m]$ to have a minimum sampling rate of $\tilde{F}_s$ and include M samples. To promote maintenance of the Nyquist criteria $\tilde{F}_s \geq F_s$ is maintained, system 110 determines M in accordance with the below equation (34):

$$M \geq \frac{\ln(1/N)}{\ln(1-1/N)} + 1. \qquad (34)$$

In this example, without following the integer constraint, an exponentially resampled signal $\tilde{x}[\tilde{n}]$ would exist across the domain $0 \leq \tilde{n} \leq \ln(N)$. To satisfy the integer constraint, system 110 determines $\tilde{n}$ in accordance with the equation shown in the below equation (35):

$$\tilde{n} = m\Lambda = m\left(\frac{\ln(N)}{M-1}\right), \qquad (35)$$
$$0 \leq m \leq M - 1.$$

Figure 2:
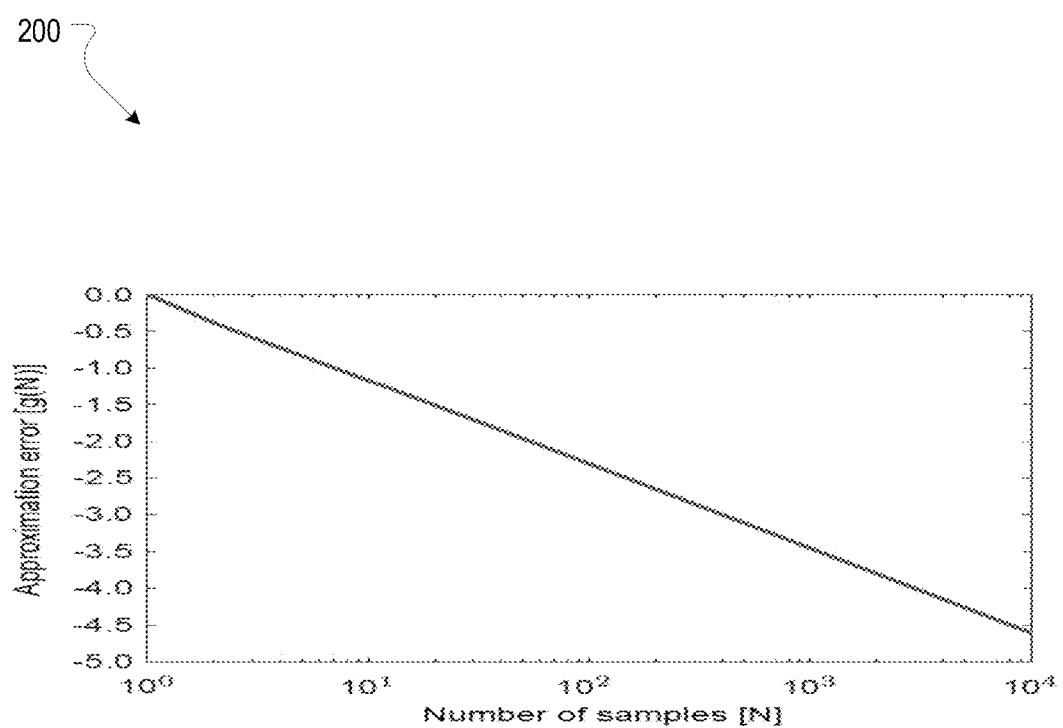
FIG. 2 shows a graph indicative of a relationship between a number of samples to resample a uniformly sampled signal and a first-order approximation.

The constant $\Lambda$ represents the sampling interval for the exponentially resampled signal. $\Lambda$ is referred to as the Mellin interval and its inverse $\Lambda^{-1}$ as the Mellin rate. To then maintain the Nyquist criteria, the minimum sampling rate in $\tilde{x}[m]$ must be greater than or equal to the Nyquist rate. This is the same as stating that maximum sampling interval, which lies between the last two samples as illustrated in FIG. 2, in $\tilde{x}[m]$ must be less than or equal to one uniform sampling interval. Following that logic, system 110 makes a determination in accordance with the below equation (36):

$$1 \geq N - \exp\left((M-2)\frac{\ln(N)}{M-1}\right) \qquad (36)$$
$$1 \geq N - N^{\frac{M-2}{M-1}}$$
$$N^{\frac{M-3}{M-1}} \geq N - 1$$

-continued $$\left(\frac{M-2}{M-1}\right)\ln(N) \geq \ln(N-1)$$

$$M(\ln(N) - \ln(N-1)) \geq 2\ln(N) - \ln(N-1)$$

$$M \geq \frac{2\ln(N) - \ln(N-1)}{\ln(N) - \ln(N-1)}$$

$$M \geq \frac{\ln(N)}{\ln\left(\frac{N}{N-1}\right)} + 1$$

$$M \geq \frac{\ln(1/N)}{\ln(1-1/N)} + 1.$$

The Mellin Resampling Theorem provides an exact bound on the number of samples necessary to exponentially resample a signal, starting from n=1, while maintaining the Nyquist criteria. In practice, M is an integer, so a ceiling operation would be applied to the result. When a signal is critically resampled in accordance with the below equation (37):

$$M = \frac{\ln(1/N)}{\ln(1-1/N)} + 1, \qquad (37)$$

the Mellin interval from equation (35) becomes $$\Lambda = -\ln(1-1/N). \qquad (38)$$

In this example, M increases with N. In this example, ln(1−1/N) is replaced with its first order Taylor series expansion −1/N. After making that substitution, the first-order approximation of equation (34)(34) becomes $$\frac{\ln(1/N)}{\ln(1-1/N)} + 1 \approx N \ln(N) + 1. \qquad (39)$$

The error function for this approximation is then defined by $$g(N) = \frac{\ln(1/N)}{\ln(1-1/N)} - N \ln(N) \qquad (40)$$
$$= -\ln(N)\left(\frac{1 + N\ln(1-1/N)}{\ln(1-1/N)}\right).$$

Assuming N>1, ln(1−1/N)<0 and N ln(1−1/N)<−1. From these inequalities, system 110 determines that the approximation error g(N)<0. In this example, under a first order approximation, $$M > N \ln(N) + 1. \qquad (41)$$

Therefore, M increases with N at a rate of approximately N ln(N). Referring to FIG. 2, diagram 200 shows the first-order approximation error curve g(N). In general, the approximation is very close, deviating by approximately 1.15 samples for every power of 10 samples N. This also demonstrates that the Mellin resampling theorem is consistent with previous results, which demonstrated that, to maintain the Nyquist criteria, M>N ln(N).

Discrete-Time Scale Transform

Using the Mellin resampling theorem in equation (34), the DTST is defined as implemented by the fast Mellin transform algorithm. In this example, $\tilde{x}[m\Lambda]$ includes the exponentially resampled and amplified signal generated from a uniformly sampled signal with a unitary sampling rate x[n], $$\tilde{x}[m\Lambda] = e^{(1/2)m\Lambda} x[e^{m\Lambda}]. \tag{42}$$

The Mellin interval $\Lambda$ is defined in equation (35). The DTST is then defined as $$S\{x[n]\} = X(e^{jc}) \tag{43}$$

$$= \sum_{m=0}^{\infty} x[m\Lambda] e^{-jct}$$

$$= \mathcal{F}\{\tilde{x}[m\Lambda]\},$$

where F now represents the DTFT of a discrete-time signal. The inverse transform can be computed by taking the inverse DTFT $$\tilde{x}[m\Lambda] = \mathcal{F}^{-1}\{X(e^{jc})\} = \int_{-\pi}^{\pi} X(e^{jc}) e^{jct} dc, \tag{44}$$

and logarithmically resampling and attenuating back to the original domain.

In another example, system 110 uses a perfect discrete-time interpolator. In this example, x̃[m] represents the energy-preserving time-skewed replica of the original uniformly sampled signal, such that $$\sum_{n=0}^{\infty} |x[n]|^2 = \Lambda \tag{45}$$

$$\sum_{m=-\infty}^{\infty} |x[\Lambda m]|^2.$$

In this example, the actual energy in the exponentially resampled signal will depend on the interpolation process used.

As in the continuous case, a scaling operation on a discrete-time signal translates to an energy-normalizing phase shift in the scale domain. For a uniformly sampled signal, a scaling operation x[βn] becomes a shift after the exponential resampling process. Therefore, in the scale domain, the scaling operation becomes $$S\{x[\beta n]\} = \mathcal{F}\{e^{(-1/2)\ln(\beta)} \tilde{x}[m\Lambda + \ln(\beta)]\} \tag{46}$$

$$= \beta^{-1/2} X(c) e^{-jc \ln(\beta)}.$$

Discrete-Time Scale Cross-Correlation Function

In this example, x[nT] and s[nT] include uniformly sampled signals with sampling interval T. The discrete-time Mellin cross-correlation between x[nT] and s[nT] is defined as $$\Phi_{xs}[\alpha] = x[nT] \diamond s_\alpha[nT], \alpha > 0 \tag{47}$$

$$= \sum_{n=0}^{\infty} x[nT] s[\alpha n T], \alpha > 0$$

-continued $$( = S^{-1}\{\overline{S\{x[nT]\}} S\{s[nT]\}\}).$$

Since T scales the signal, it translates to a phase shift in the scale domain so that $$\Phi_{xs}[\alpha] = S^{-1}\{\overline{\mathcal{L}\{x[nT]\}} T^{-1/2} e^{-jc \ln(T)} S\{s[n]\} T^{-1/2} e^{jc \ln(T)}\} \tag{48}$$

$$= T^{-1} S^{-1}\{\overline{S\{x[nT]\}} S\{s[n]\}\}.$$

In an example, discrete-time scale cross-correlation is defined from the pair of exponentially resampled and amplified signals, in accordance with the below equations:

$$\tilde{x}[m\Lambda] = e^{(1/2)m\Lambda} x[e^{m\Lambda}] \tag{49}$$

$$\tilde{s}[m\Lambda] = e^{(1/2)m\Lambda} s[e^{m\Lambda}], \tag{50}$$

where $\Lambda$ is the Mellin interval defined in (38). From these signals, system 110 determines the exponentially-skewed scale cross-correlation function, in accordance with the below equation (51):

$$\Phi_{xs}[k\Lambda] = T^{-1} e^{-(1/2)k\Lambda} \sum_{m=-\infty}^{\infty} \tilde{x}[m\Lambda] \tilde{s}[m\Lambda + k\Lambda] \tag{51}$$

$$= T^{-1} e^{-(1/2)k\Lambda} F^{-1}\{\overline{\mathcal{F}\tilde{x}[m\Lambda]} \mathcal{F}\{\tilde{s}[m\Lambda]\}\}$$

$$= T^{-1} e^{-(1/2)k\Lambda} F^{-1}\{\overline{S\{x[n]\}} S\{s[n]\}\}$$

$$= e^{-(1/2)k\Lambda} \Psi_{xs}[k\Lambda],$$

where $k\Lambda = \ln(\alpha)$. System 110 defines $\Psi_{xs}[k\Lambda]$ to be the exponential-time cross-correlation function in discrete time, $$\Psi_{xs}[k\Lambda] = F^{-1}\{\overline{S\{x[nT]\}} S\{s[nT]\}\}. \tag{52}$$

Figure 4:
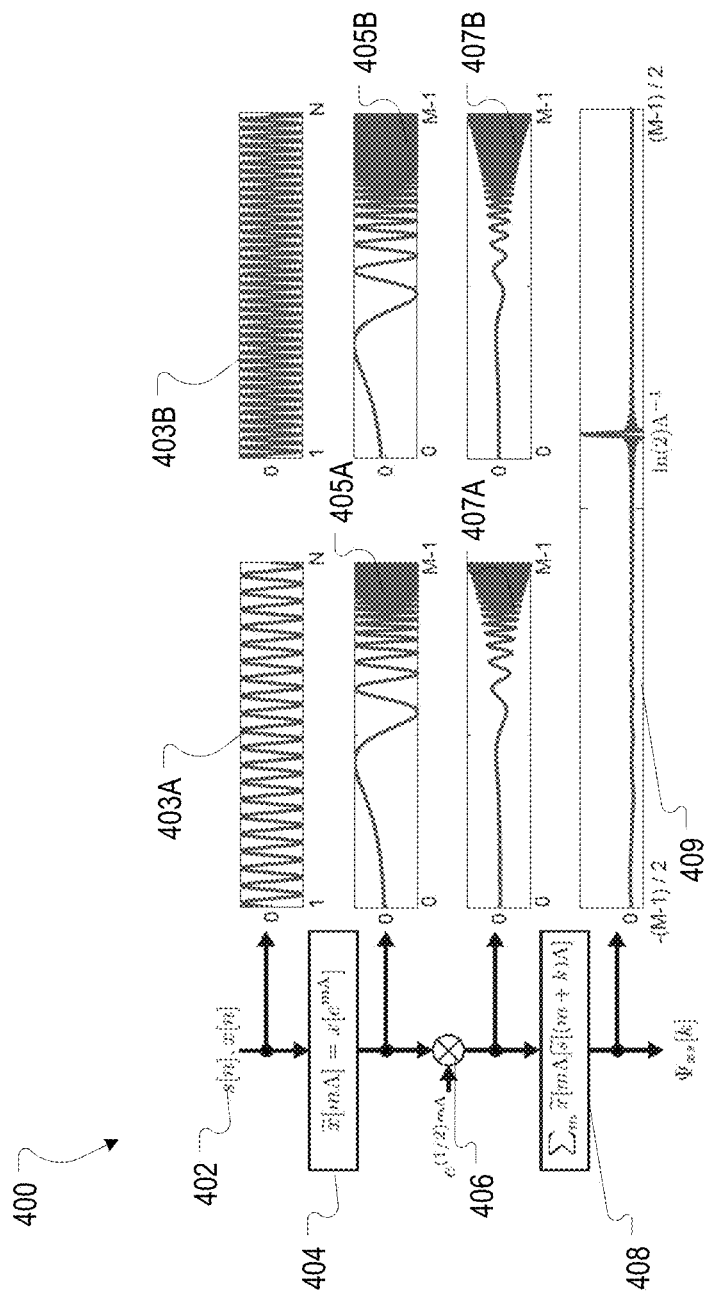
FIG. 4 shows a diagram that demonstrates actions in computing the discrete-time exponential-time cross-correlation.

If [m$\Lambda$] and [m$\Lambda$] are nonzero within the range $0 \leq m \leq M-1$, then $\Phi xs[k\Lambda]$ and $\Psi xs[k\Lambda]$ will be nonzero over $-(M-1) \leq k \leq M-1$. Direct computation of the scale cross-correlation $\Phi xs[\alpha]$ requires implementation of the inverse scale transform, and therefore a logarithmic decimation of $\Phi xs[k\Lambda]$. However, $\Psi xs[k\Lambda]$ is not a causal signal, an assumption made by the Mellin resampling theorem. In an example, system 110 computes the scale factor and scale-invariant correlation coefficient between two signals directly from $\Psi xs[k\Lambda]$. Referring to FIG. 4, process 400 illustrates actions in the computation of the $\Psi xs[k\Lambda]$ from two windowed sinusoids, which vary by a scale factor of 2. In this example, system 110 receives (402) sinusoids 403a, 403b. Sinusoid 403a oscillates at 20 Hz. Sinusoid 403b oscillates at 40 Hz. System 110 exponentially resamples (404) sinusoids 403a, 403b, resulting in signals 405a, 405b, respectively. System 110 multiples (406) the resampled sinusoids by an exponential amplification factor, resulting in signals 407a, 407b, respectively. System 110 also cross-correlates (408) the multiplied, resampled sinusoids with each other, resulting in signal 409.

Discrete-Time Scale Factor Computation

In this example, x[n] and s[n] include scaled replicas of each other such that x[n]=s[βn]. After exponentially resampling and amplifying the signals, the scale becomes a shift $$\tilde{s}[m\Lambda] = e^{(1/2)m\Lambda} s[e^{m\Lambda}]$$

$$\tilde{x}[m\Lambda] = (\beta)^{-1/2} \tilde{s}[m\Lambda + \ln(\beta)] \tag{53}$$

Under these circumstances, system 110 applies the Cauchy-Schwarz inequality to the exponential-time cross-correlation function $\Psi_{xs}[k\Lambda]$ in equation (52), $$\frac{1}{T^2\beta}\left|\sum_{m=-\infty}^{\infty} \tilde{s}[m\Lambda + \ln(\beta)]\tilde{s}[(m+k)\Lambda]\right|^2 \leq \quad (54)$$

$$\frac{1}{T^2\beta}\sum_{m=-\infty}^{\infty} |\tilde{s}[m\Lambda + \ln(\beta)]|^2 \cdot \sum_{m=-\infty}^{\infty} |\tilde{s}[(m+k)\Lambda]|_2 =$$

$$\frac{1}{T^2\beta}\left|\frac{1}{\Lambda}\sum_{m=-\infty}^{\infty} |\tilde{s}[m]|^2\right|^2.$$

Assuming $s[m\Lambda]$ is not a periodic function, the expressions in equation (54) will be equal when $k\Lambda=\ln(\beta)$. This implies that, for non-periodic functions, the scale cross-correlation has a unique maximum when $$\operatorname*{argmax}_{k} \Psi_{xs}[k\Lambda] = \ln(\beta)\Lambda^{-1}. \quad (55)$$

Through algebraic manipulation, this concludes that the scale factor is equal to $$\beta = \exp\left(\Lambda \operatorname*{argmax}_{k} \Psi_{xs}[k\Lambda]\right). \quad (56)$$

The function $\Psi_{xs}[k\Lambda]$ is generally not convex. Therefore, when implementing, care must be taken to compute the maximum.

Discrete-Time Scale-Invariant Correlation Coefficient

For simplicity, assume both $s[nT]$ and $x[nT]$ are zero-mean signals so that their exponentially resampled versions $\tilde{s}[m\Lambda]$ and $\tilde{x}[m\Lambda]$ are also zero-mean. From the Cauchy-Schwarz inequality in equation (52), system 110 determines the maximum value of the exponential-time cross-correlation $\Psi_{xs}[k\Lambda]$ in accordance with the below equation (55):

$$\max_{k} \Psi_{xs}(k\Lambda) = \frac{1}{T\Lambda\sqrt{\beta}} \sum_{m=-\infty}^{\infty} |\tilde{s}[m]|^2 \quad (57)$$

$$= \frac{1}{T}\sqrt{\sum_{m=-\infty}^{\infty} |\tilde{s}[m\Lambda]|^2} \cdot \sqrt{\sum_{m=-\infty}^{\infty} |\tilde{x}[m\Lambda]|^2}$$

$$= \frac{1}{T}\sigma_{\tilde{s}}\sigma_{\tilde{x}}$$

System 110 computes the discrete-time scale-invariant correlation coefficient the in accordance with the below equation (58):

$$\psi_{xs} = \frac{T}{\sigma_{\tilde{s}}\sigma_{\tilde{x}}}\left(\max_{k}\Psi_{xs}(k\Lambda)\right), \quad (58)$$

As in continuous time, $\psi_{xs}$ is 1 when $x[nT]=s[\beta nT]$, $\psi_{xs}$ is −1 when $x[nT]=-s[\beta nT]$, and there is no scale relationship between the two signals when $\psi_{xs}=0$. System 110 uses the values between the extrema to determine the degree scale-invariant linear correlation between the two signals.

Simulation Setup and Methodology

In an example, system 110 is configured to compare the scale cross-correlation, LPC, and OSS compensation techniques using ultrasonic data from a thin plate under variable temperature conditions. To produce guided waves, system 110 uses a pair of synchronized lead zirconate titanate (PZT) piezoelectric transducers permanently bonded to the surface of a 9.8 cm wide by 30.5 cm long by 0.1 cm aluminum plate. Signals were generated and measured at a sampling rate of 1 MHz using a National Instruments PXI data acquisition equipment. For each measurement, the transducers were driven using a wide-band impulse-like sinc excitation and its response recorded for 10 ms. Referring to FIGS. 8A, 8B, diagrams 800, 802 show the excitation of a time domain signal and a power spectral density, respectively. Referring to FIGS. 9A, 9B, diagrams 900, 902 show the response (to excitation) of a time domain signal and a power spectral density, respectively.

Figure 6:
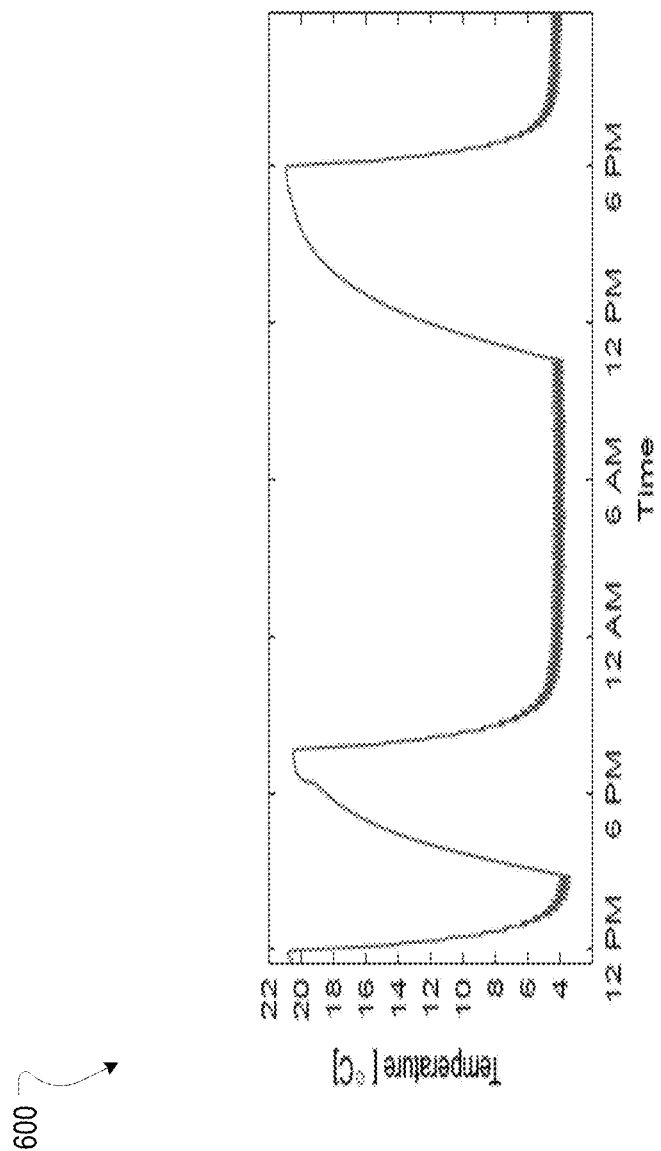
FIG. 6 shows a graph of measured ambient temperatures during a simulation.

The experiment ran for 36.3 hours between 11:30 AM and 11:50 PM of the following day. During this time, the aluminum plate was cooled and warmed in a refrigerator while guided waves were generated and automatically recorded by the transducers at 2 minute intervals. The ambient temperature within the refrigerator was also measured automatically at 1 minute intervals. Referring to FIG. 6, graph 600 shows the measured ambient temperature over time. Starting at 11:30 AM on day one, the temperature was gradually reduced from room temperature, 20.5° C., to 3.37° C. until 2:51 PM. Between 2:51 PM and 7:33 PM, the temperature was then gradually increased back to room temperature, 20.4° C. After 7:33 PM, the ambient temperature decreased and then remained relatively constant, at around 3.89° C., between midnight and 10:36 AM the next day. Between 10:36 AM and 5:56 PM, the temperature was again gradually increased to 20.94° C. and then gradually decreased to 4.17° C. until 11:50 PM, when the experiment ended.

At 6:18 PM on the first day, a cylindrical, steel, greased-coupled mass with a diameter of 3.8 cm and a length of 4.5 cm, was placed on top of the aluminum plate to simulate damage. At 4:04 PM on the second day, the mass was removed from the plate. The mass was removed to confirm that the changes in the wave propagation were a result of the mass and not an artifact introduced by the placement procedure. The timing also allowed us to measure both an increase and decrease in temperature with and without the mass present. Using a mass in place of damage allows easy repeatability of the experiment. While the mass may not perfectly simulate damage, it changes the propagation environment in ways that temperature will not. In this way, the mass acts similar to damage.

An impulsive signal was chosen in order to drive the PZT transducers to excite as wide a frequency band as possible. Signal scaling occurs in both the time and frequency domains. Therefore, limiting the observable frequencies will reduce the accuracy of the uniform scaling model used by the temperature compensation strategies.

After recording each guided wave record, the signals are high-pass filtered with a 3 kHz cutoff frequency and advanced 0.5 ms. The high-pass filtering operation in done to remove systematic low frequency noise in the system. This noise arises from various sources, such as mechanical vibrations and the pyroelectric effect. The time shift operation is necessary to remove group delay introduced by the excitation signal. Failing to account for group delay will introduce errors into the compensation strategies since the scaling origin will then not be located at $t=0$.

Correlation Analysis

System 110 compares five different descriptors used for detecting the mass: the correlation coefficient, the OSS correlation coefficient, two variations on the LPC correlation coefficient, and the scale-invariant correlation coefficient. The correlation coefficient is a standard measure of similarity but is very sensitive to changes in scale. In contrast, the OSS, LPC, and scale-invariant correlation coefficients are scale-invariant measures and more robust to changes in temperature.

For each LPC method, system 110 utilizes a different form of linear regression. The first uses a standard least-squares linear regression to estimate the scale factor. The second LPC method uses a robust linear regression method using MATLAB's robustfit function. This function performs an iteratively reweighted least-squares regression, which is more robust to outlier data. In implementing each LPC method, system 110 uses a local window size of 1000 samples with a hop size of 1 sample between each cross-correlation operation. A larger hop size would increase the computational speed of the technique, but the hop size was kept to a minimum to maximize the accuracy of the linear regression. In computing the OSS correlation coefficient, system 110 accesses a library of 200 baselines over a scale range of 0.99 to 1.01, which is reasonable for this application. The library was designed to have the same resolution as the scale cross-correlation.

Figure 7A:
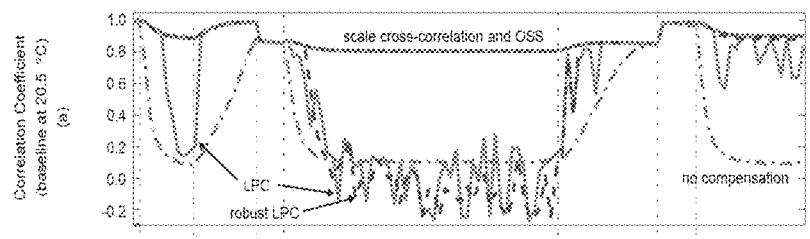
FIGS. 7A-7D show correlation coefficients for temperature compensation methods.
Figure 7B:
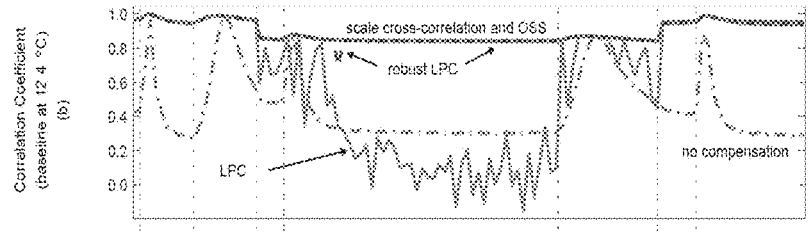

Referring to FIGS. 7A, 7B, graphs 700, 702 show the correlation coefficients computed over the course of the experiment for two different baseline signals, taken at 20.5° C. and 12.4° C. respectively. The first baseline is near the highest temperature measured and the second is approximately the median temperature. Two baselines illustrate how each method is affected by different ranges of temperature change. In both plots, the standard correlation coefficient, labeled "no compensation," is significantly affected by temperature. As the temperature deviates from the baseline temperature, the correlation coefficient decreases significantly. However, when the mass is added or removed, the correlation coefficient shows minor changes.

The introduction of the mass causes significant changes for each of the compensated correlation coefficients. However, the LPC correlation coefficients are significantly affected by other effects as well. In FIG. 7A and FIG. 7B, the LPC correlation coefficients are almost equal to the OSS and scale-invariant correlation coefficients when the temperature is close to the baseline temperature. However, when the temperature deviates too far from the baseline, the LPC correlation coefficients drop and vary erratically. When the mass is on the plate, this erratic behavior becomes even more prevalent.

The OSS and scale-invariant correlation coefficients of vary significantly at the moment the mass is introduced. The two techniques are almost equal to each other throughout the experiment. However, both descriptors, as well as LPC, do vary weakly with temperature. This indicates that it may be difficult to distinguish the mass from a sharp change in temperature using the compensated correlation coefficients alone. By utilizing both these scale-invariant descriptors as well as an estimate of the scale change, system 110 has an improved ability to detect the mass.

Temperature and Scale

Figure 7C:
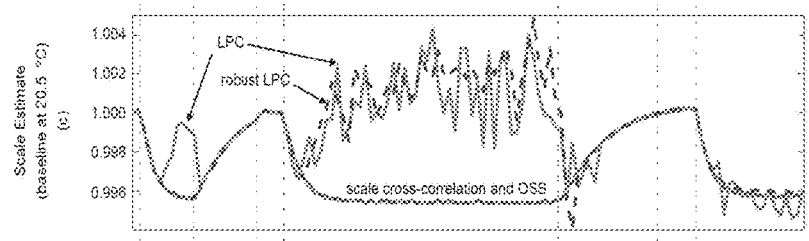
Figure 7D:
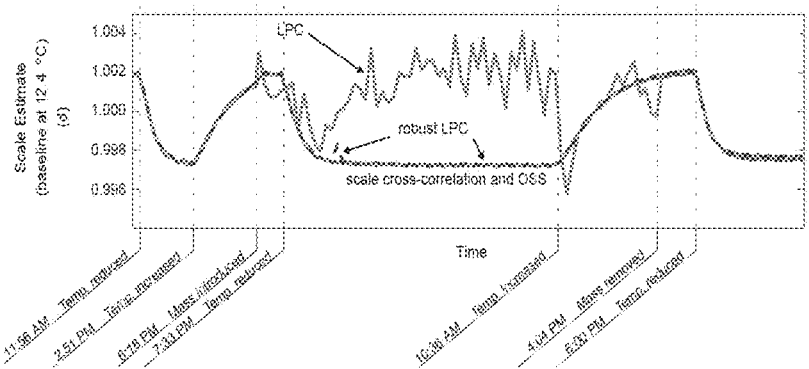

Referring to FIGS. 7C and 7D, graphs 704, 706 show the scale factor estimates for each observed signal relative to two baseline signals. Graph 704 illustrates scale estimates with baseline at 20.5° C. Graph 706 illustrates scale estimates with baseline at 13.1° C.

Each temperature compensation method is associated with an estimate. Comparison of FIGS. 7A-7D with FIG. 6 shows that the scale estimates from OSS and the scale cross-correlation follow a similar trend as the ambient temperature. The LPC technique estimate, however, is a poor predictor of temperature when the current temperature is far from the baseline temperature and when the mass is on the specimen. As with the correlation results, the OSS and scale cross-correlation produce almost identical results, and the scale estimates are not largely affected by the addition or removal of the mass.

Figure 10:
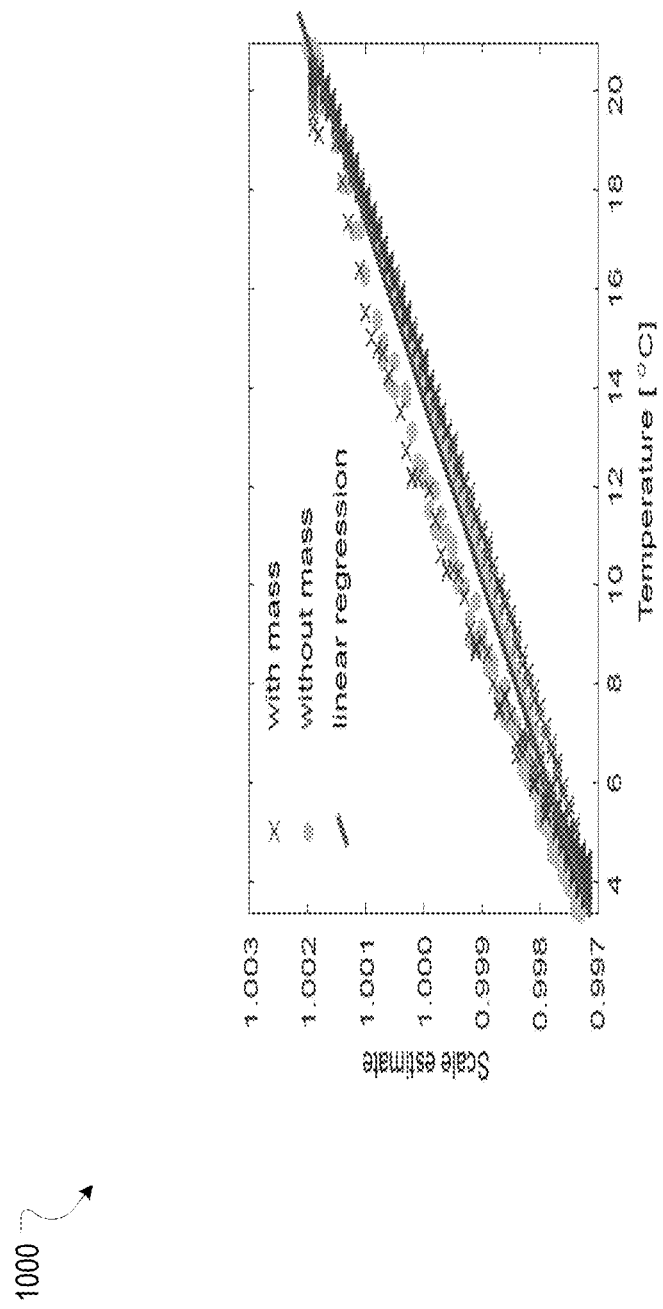
FIG. 10 shows correlation coefficients versus scale cross-correlation scale estimates.

Referring to FIG. 10, graph 1000 shows the relationship between scale and temperature to be approximately linear, regardless of the state of the mass. The data, however, does exhibit a hysteresis, in which the scale value transitions slower than the temperature. This phenomenon is a result of the temperature sensor recording the ambient temperature rather than the temperature of the specimen. The temperature of the metal specimen changes at a slower rate than the air surrounding it. Therefore the speed of the guided waves, and scale change in the signal, will change slower than the temperature as recorded by the sensor.

Mass Classification

As illustrated in the FIGS. 7A-7B, the scale-invariant correlation coefficient is not perfectly invariant to temperature. However, in FIGS. 7C-7D, the scale estimate is affected by temperature. Therefore, the combination of these two descriptors can be used to provide a more complete description of the system than either one alone.

Figure 11:
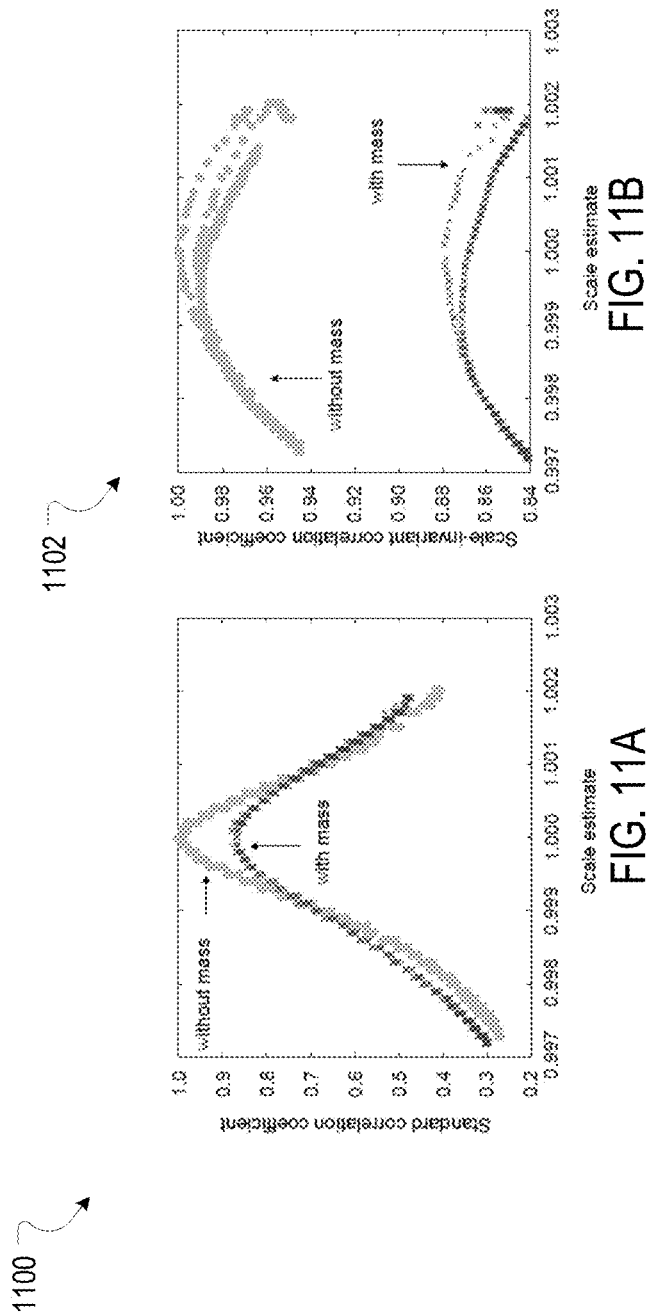
FIGS. 11A, 11B are examples of graphs that illustrate the relationships between the standard and compensated correlation coefficients and the scale estimates.

FIGS. 11A, 11B illustrate the relationships between the standard and compensated correlation coefficients and the scale estimates, using a baseline signal at 13.1° C. Referring to FIG. 11A, graph 1100 shows the relationship between scale, estimated using the scale cross-correlation, and the standard correlation coefficient without temperature compensation. In this plot, there are little separation between the data taken with the mass present and the data taken without the mass. Referring to FIG. 11B, graph 1102 illustrates the relationship between the scale-invariant correlation coefficient and its associated scale estimate. In this plot, there is a clear separation between the data taken with and without the mass. Given a linear discriminator, the two conditions can be classified with one hundred percent accuracy. Using both the scale-invariant correlation coefficient and scale estimate allows us to better differentiate model errors caused by temperature and more significant deviations caused by damage or other effects. In this example, the two curves may eventually meet. This implies that, as the temperature deviates further from the baseline, the mass will become increasingly more difficult to detect.

Figure 5:
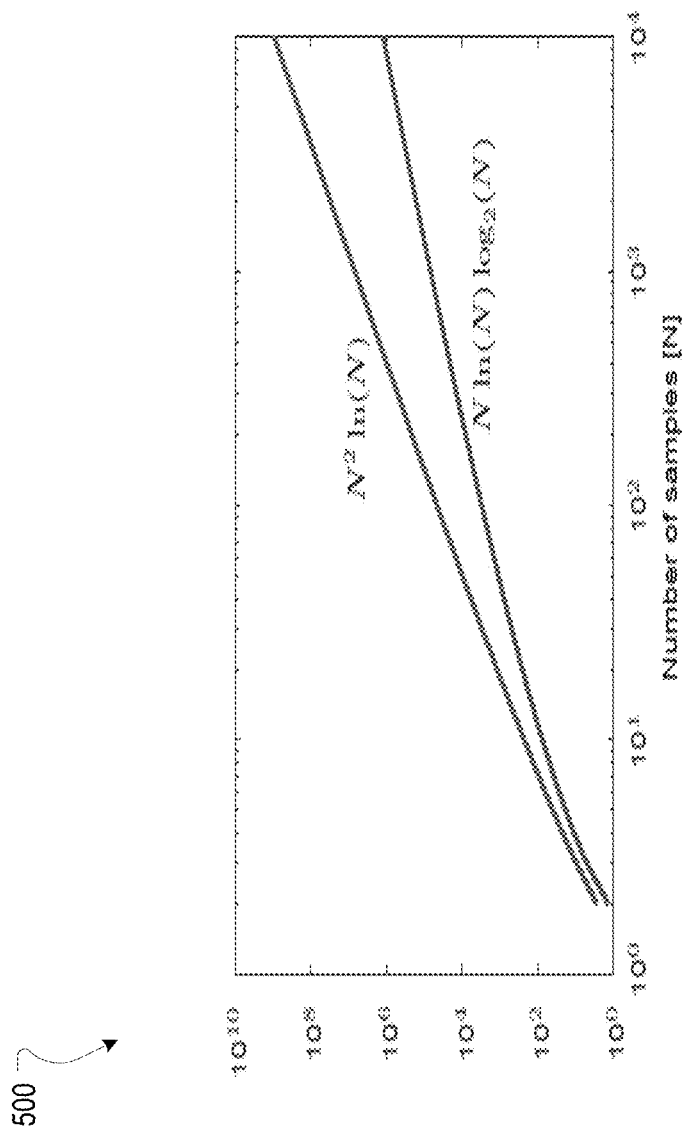
FIG. 5 shows curves demonstrating the computational growth rates of OSS ($N^2 \ln(N)$) and the scale cross-correlation ($N \ln(N) \log_2 (N)$).

System 110 implements a computationally efficient technique, the scale cross-correlation function, for analyzing the scaling behavior between two signals. Through analytical and experimental comparison with the optimal signal stretch method, the scale cross-correlation is an optimal (minimum mean squared error) temperature compensation method, for a uniform scaling model for temperature. Given a baseline and observed signal, system 110 computes the scale factor and the scale-invariant correlation coefficient between them. The computation is presented for continuous-time and discrete time systems. In discrete time, system 110 derives the Mellin resampling theorem, which states the minimum number of samples necessary to exponentially resample a uniformly sampled signal. FIG. 5 shows curves in graph 500 demonstrating the computational growth rates of OSS ($N^2 \ln(N)$) and the scale cross-correlation ($N \ln(N) \log 2(N)$).

The estimate of the scale factor is a robust, linear predictor of temperature in the system. The scale-invariant correlation coefficient was shown to be approximately invariant to variations in temperature. Using both the scale factor and scale-invariant correlation coefficient, a mass, simulating damage, could be detected with a linear discriminator.

Since the scale cross-correlation requires no dense baseline library, it is a potentially very flexible tool for temperature compensation. Furthermore, its close relationship with the Fourier transform demonstrates it to be a potentially powerful tool as well.

Figure 12:
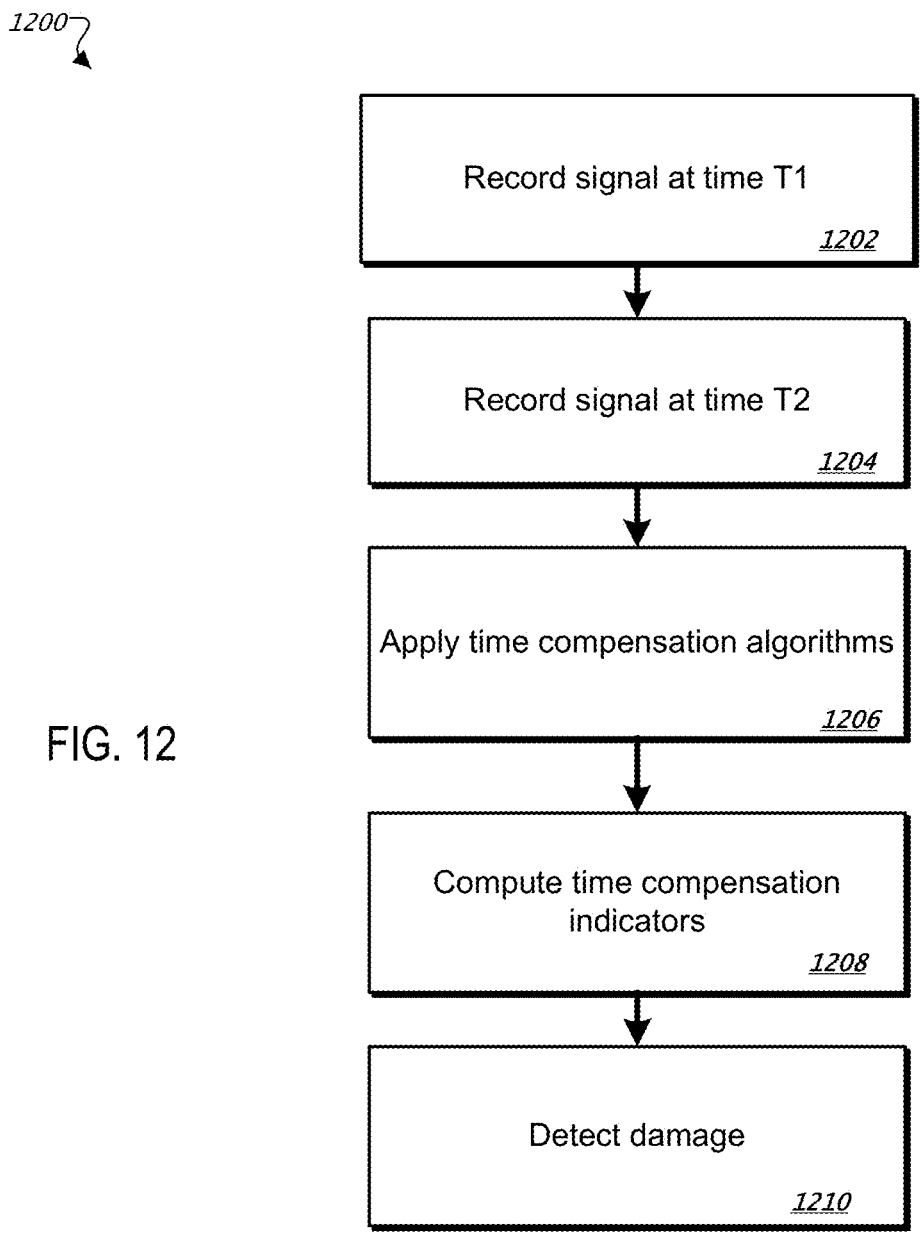
FIG. 12 is a flowchart of a process for generating temperature compensation indicators.

Referring to FIG. 12, system 110 executes process 1200 in computing temperature compensation indicators, e.g., a scale factor, a scale invariant correlation coefficient, and so forth. In operation, system 110 records (1202) a signal at a first point in time. The record signaled may include waveform data. The record signal is a signal that has travelled through a structure. At a second point in time, system 110 records (1204) another signal that has travelled through the structure. Between the first point in time and the second point in time, the structure has experienced one or more structure changes (e.g., damage or other structural modifications).

Using the recorded signals, system 110 applies (1206) one or more time compensation algorithms, including, e.g., an algorithm for computing the scale cross-correlation function (from the scale transform), an algorithm for computing the scale factor (e.g., from the scale cross-correlation function), an algorithm for computing the scale-invariant correlation coefficient (e.g., from the scale cross-correlation function), and so forth. System 110 computes (1208) time compensation indicators, e.g., using the time compensation algorithms. System 110 computes various types of time compensation indicators, including, e.g., a scale factor, a scale-invariant correlation coefficient, and so forth. Using the time compensation indicators, system 110 detects (1210) damage in the structure. For example, system 110 applies the computed time compensation indicators to the record signals to correct and/or identify variations in the signals that are caused by temperature fluctuations between times T1, T2. After identifying the variations that are caused by temperature fluctuations, system 110 identifies other variations in the signals, with these other variations being indicative of structural changes in the structure.

Referring to FIG. 13, components 1300 of an environment (e.g., environment 100) for generating temperature compensation indicators. Client device 101 can be any sort of computing device capable of taking input from a user and communicating over a network (not shown) with system 110 and/or with other client devices. In an example, client device 101 is a device associated with structure 102 (FIG. 1) for recording and/or tracking traversal of a signal through structure 102. For example, client device 101 can be a mobile device, a desktop computer, a laptop, a personal digital assistant ("PDA"), a server, an embedded computing system, a mobile device and so forth. Client device 101 can include monitor 1108, which renders visual representations of interface 1106.

System 110 can be any of a variety of computing devices capable of receiving data, such as a server, a distributed computing system, a desktop computer, a laptop, a cell phone, a rack-mounted server, and so forth. System 110 may be a single server or a group of servers that are at a same location or at different locations.

System 110 can receive data from client device 101 via interfaces 1106, including, e.g., graphical user interfaces. Interfaces 1106 can be any type of interface capable of receiving data over a network, such as an Ethernet interface, a wireless networking interface, a fiber-optic networking interface, a modem, and so forth. System 110 also includes a processor 1002 and memory 1004. A bus system (not shown), including, for example, a data bus and a motherboard, can be used to establish and to control data communication between the components of server 110. In the example of FIG. 13, memory 1004 includes data engine 1302 for executing the techniques and operations described herein.

Processor 1002 may include one or more microprocessors. Generally, processor 1002 may include any appropriate processor and/or logic that is capable of receiving and storing data, and of communicating over a network (not shown). Memory 1004 can include a hard drive and a random access memory storage device, such as a dynamic random access memory, machine-readable media, or other types of non-transitory machine-readable storage devices. Components 1300 also include data repository 114, which is configured to store data collected through system 110 and generated by system 110.

Embodiments can be implemented in digital electronic circuitry, or in computer hardware, firmware, software, or in combinations thereof. Apparatus of the invention can be implemented in a computer program product tangibly embodied or stored in a machine-readable storage device and/or machine readable media for execution by a programmable processor; and method actions can be performed by a programmable processor executing a program of instructions to perform functions and operations of the invention by operating on input data and generating output.

The techniques described herein can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Computer readable storage media are storage devices suitable for tangibly embodying computer program instructions and data include all forms of volatile memory such as RAM and non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

Other embodiments are within the scope and spirit of the description claims. In another example, due to the nature of software, functions described above can be implemented using software, hardware, firmware, hardwiring, or combinations of any of these. Features implementing functions may also be physically located at various positions, including being distributed such that portions of functions are implemented at different physical locations.

A number of embodiments have been described. Nevertheless, it will be understood that various modifications can be made without departing from the spirit and scope of the processes and techniques described herein. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A method for detecting an anomaly in a physical structure, the method comprising:
    causing ultrasonic transmission, through and across a wall or boundaries of a physical structure, of a first signal comprising a first guided wave, and a second signal comprising a second guided wave;
    obtaining a first sequence of data representing a traversal of the first signal through and across the wall, plate, or boundary of the physical structure at a first time, wherein a first ambient temperature is associated with the structure at the first time;
    obtaining a second sequence of data representing a traversal of the second signal through and across the wall or boundaries of the physical structure at a second time, wherein a second ambient temperature is associated with the physical structure at the second time, the first ambient temperature differs from the second ambient temperature, and a difference between the first ambient temperature and the second ambient temperature causes a distortion of the second signal, relative to the first signal, as the second signal traverses through and across the wall or boundaries of the physical structure;
    applying a scale transform to the first sequence of data and the second sequence of data;
    computing, by a processing device and based on applying the scale transform, a scale-cross correlation function that promotes identification of scaling behavior between the first sequence of data and the second sequence of data, wherein a computational complexity of computing the scale cross-correlation function includes a log-linear complexity;
    performing at least first operations or second operations;
    with the first operations comprising:
        computing, by the processing device and based on the scale-cross correlation function, a scale factor for the first sequence of data and the second sequence of data, with the scale factor being indicative of an amount of variation between the first ambient temperature and the second ambient temperature;
        applying the scale factor to the second sequence of data to produce a third sequence of data representing the traversal of the second signal through and across the wall or boundaries of the physical structure at the second time, the third sequence of data representing the second signal adjusted based on the scale factor to compensate for the distortion of the second signal, relative to the first signal, that results from variation in the first ambient temperature and the second ambient temperature; and
        generating a compensated signal based on the third sequence of data, the compensated signal comprising a resolution fidelity that is maintained from a resolution fidelity of the second signal;
    with the second operations comprising:
        computing, by the processing device and based on the scale-cross correlation function, a scale invariant correlation coefficient between the first sequence of data and the second sequence of data, with the scale invariant correlation coefficient comprising a compensation statistic for compensating for the distortion of the second signal, relative to the first signal, that results from variation in the first ambient temperature and the second ambient temperature;
        applying the scale invariant correlation coefficient comprising the compensation statistic to the second sequence of data to produce the third sequence of data representing the traversal of the second signal through and across the wall or boundaries of the physical structure at the second time, the third sequence of data representing the second signal adjusted based on the compensation statistic for the distortion of the second signal, relative to the first signal, that results from variation in the first ambient temperature and the second ambient temperature; and
        generating the compensated signal based on the third sequence of data, the compensated signal comprising the resolution fidelity that is maintained from the resolution fidelity of the second signal; and
    detecting an anomaly in the wall or between the boundaries of the physical structure based on a comparison of the compensated signal to the first signal.

2. The computer-implemented method of claim 1, further comprising:
    detecting, based on the scale factor and the scale invariant correlation coefficient, one or more areas of structural change in the wall or between the boundaries of the physical structure.

3. The computer-implemented method of claim 2, wherein the structural change comprises a degradation of the wall or between the boundaries of the physical structure.

4. The computer-implemented method of claim 1, wherein the scale invariant correlation coefficient is indicative of a measure of similarity between the first sequence of data and the second sequence of data.

5. The computer-implemented method of claim 1, wherein the scale factor comprises a value that is used as a multiplier in scaling the first sequence of data to correspond to the second sequence of data.

6. The method of claim 1, wherein the processing device is included in a wave-based damage detection system.

7. The method of claim 1, wherein the physical structure comprises a concrete structure.

8. The method of claim 1, wherein the scale-cross correlation function is computed in accordance with:

$$x(t) \diamond s_\alpha(t) = S^{-1}\{\overline{S\{x(t)\}} S\{s(t)\}\},$$

wherein $\diamond$ represents a scale cross-correlation operation;
wherein the overbar represents a complex conjugation operation;
wherein $x(t)$ is the first sequence of data;
wherein $s(t)$ is the second sequence of data;
wherein $\alpha$ includes a scaling factor on $s(t)$;
wherein $S\{x(t)\}$ is the scale domain of $x(t)$;
wherein $S\{s(t)\}$ is the scale domain of $s(t)$; and
wherein $S^{-1}\{\cdot\}$ *represents an inverse scale transform.*

9. The method of claim 1, wherein computing the scale-cross correlation function comprises:

computing a product of a scale domain of the first sequence of data and a scale domain of the second sequence of data.

10. The method of claim 1, wherein computing the scale-cross correlation function comprises:
resampling the first sequence of data;
resampling the second sequence of data;
applying an amplification factor to the resampled first and second sequence of data; and
cross-correlating the amplified, resampled first and second sequence of data.

11. The method of claim 1, wherein computing the scale-invariant correlation coefficient comprises:
determining an increased value of the scale cross-correlation function in a stretch domain factor, relative to other values of the scale cross-correlation function in the stretch domain factor.

12. The method of claim 1, wherein one or more of the first signal and the second signal is an ultrasonic wave signal.

13. The method of claim 1, wherein the physical structure comprises one or more of a pipe structure, a heating structure, one or more pipe structures in an oil refinery, one or more pipe structures in a chemical refinery, one or more pipe structures in a gas refinery, one or more natural fuse pipelines, one or more oil pipelines, one or more heating pipe structures, one or more cooling pipe structures, one or more pipe structures in a nuclear power plant, one or more pressure vessels, one or more concrete structures of a bridge, one or more concrete structures of civil infrastructure, one or more portion of an airplace, one or more portions of an aerospace vehicle, one or more portions of a submarine, and one or more metallic structures.

14. The method of claim 1, further comprising:
identifying a maximization of the scale-cross correlation function in the stretch factor domain;
wherein computing the scale factor comprises:
computing, by the processing device and based on the maximization of the scale-cross correlation function in the stretch factor domain, the scale factor for the first sequence of data and the second sequence of data; and
wherein computing the scale invariant correlation coefficient comprises:
computing, by the processing device and based on the maximization of the scale-cross correlation function in the stretch factor domain, the scale invariant correlation coefficient between the first sequence of data and the second sequence of data.

15. The method of claim 1, further comprising:
identifying a maximization of the scale-cross correlation function in the scale transform domain;
wherein computing the scale factor comprises:
computing, by the processing device and based on the maximization of the scale-cross correlation function in the scale transform domain, the scale factor for the first sequence of data and the second sequence of data; and
wherein computing the scale invariant correlation coefficient comprises:
computing, by the processing device and based on the maximization of the scale-cross correlation function in the scale transform domain, the scale invariant correlation coefficient between the first sequence of data and the second sequence of data.

16. An apparatus for detecting an anomaly in a physical structure, the apparatus comprising:
one or more processing devices; and
one or more machine-readable hardware storage devices storing instructions that are executable to cause the one or more processing devices to perform operations comprising:
causing guided wave transmission, through a physical structure, of a first signal and a second signal;
obtaining a first sequence of data representing a traversal of the first signal through the physical structure at a first time, wherein a first ambient temperature is associated with the physical structure at the first time;
obtaining a second sequence of data representing a traversal of the second signal through the physical structure at a second time, wherein a second ambient temperature is associated with the physical structure at the second time, the first ambient temperature differs from the second ambient temperature, and a difference between the first ambient temperature and the second ambient temperature causes a distortion of the second signal, relative to the first signal, as the second signal traverses through the physical structure;
applying a scale transform to the first sequence of data and the second sequence of data;
computing, based on applying the scale transform, a scale-cross correlation function that promotes identification of scaling behavior between the first sequence of data and the second sequence of data, wherein a computational complexity of computing the scale cross-correlation function includes a log-linear complexity;
performing at least first operations or second operations;
with the first operations comprising:
computing, based on the scale-cross correlation function, a scale factor for the first sequence of data and the second sequence of data, with the scale factor being indicative of an amount of variation between the first ambient temperature and the second ambient temperature;
applying the scale factor to the second sequence of data to produce a third sequence of data representing the traversal of the second signal through the physical structure at the second time, the third sequence of data representing the second signal adjusted based on the scale factor to compensate for the distortion of the second signal, relative to the first signal, that results from variation in the first ambient temperature and the second ambient temperature; and
generating a compensated signal based on the third sequence of data, the compensated signal comprising a resolution fidelity that is maintained from a resolution fidelity of the second signal;
with the second operations comprising:
computing, based on the scale-cross correlation function, a scale invariant correlation coefficient between the first sequence of data and the second sequence of data, with the scale invariant correlation coefficient comprising a compensation statistic for compensating for the distortion of the second signal, relative to the first signal, that results from variation in the first ambient temperature and the second ambient temperatures;
applying the scale invariant correlation coefficient comprising the compensation statistic to the second sequence of data to produce the third sequence of data representing the traversal of the second signal through the physical structure at the second time, the third sequence of data representing the second signal adjusted based on the compensation statistic for the distortion of the second signal, relative to the first signal, that results from variation in the first ambient temperature and the second ambient temperature; and generating the compensated signal based on the third sequence of data, the compensated signal comprising the resolution fidelity that is maintained from the resolution fidelity of the second signal.

17. The apparatus of claim 16, wherein the operations further comprise:

detecting, based on the scale factor and the scale invariant correlation coefficient, one or more areas of structural change in the physical structure.

18. One or more machine-readable hardware storage devices storing instructions that are executable to cause one or more processing devices to perform operations comprising:

causing guided wave transmission, through a physical structure, of a first signal and a second signal;

obtaining a first sequence of data representing a traversal of the first signal through the physical structure at a first time, wherein a first ambient temperature is associated with the physical structure at the first time;

obtaining a second sequence of data representing a traversal of the second signal through the physical structure at a second time, wherein a second ambient temperature is associated with the physical structure at the second time, the first ambient temperature differs from the second ambient temperature, and a difference between the first ambient temperature and the second ambient temperature causes a distortion of the second signal, relative to the first signal, as the second signal traverses through the physical structure;

applying a scale transform to the first sequence of data and the second sequence of data;

computing, based on applying the scale transform, a scale-cross correlation function that promotes identification of scaling behavior between the first sequence of data and the second sequence of data, wherein a computational complexity of computing the scale cross-correlation function includes a log-linear complexity;

performing at least first operations or second operations; with the first operations comprising:

computing, based on the scale-cross correlation function, a scale factor for the first sequence of data and the second sequence of data, with the scale factor being indicative of an amount of variation between the first ambient temperature and the second ambient temperature;

applying the scale factor to the second sequence of data to produce a third sequence of data representing the traversal of the second signal through the physical structure at the second time, the third sequence of data representing the second signal adjusted based on the scale factor to compensate for the distortion of the second signal, relative to the first signal, that results from variation in the first ambient temperature and the second ambient temperature; and generating a compensated signal based on the third sequence of data, the compensated signal comprising a resolution fidelity that is maintained from a resolution fidelity of the second signal;

with the second operations comprising:

computing, based on the scale-cross correlation function, a scale invariant correlation coefficient between the first sequence of data and the second sequence of data, with the scale invariant correlation coefficient comprising a compensation statistic for compensating for the distortion of the second signal, relative to the first signal, that results from variation in the first ambient temperature and the second ambient temperature;

applying the scale invariant correlation coefficient comprising the compensation statistic to the second sequence of data to produce the third sequence of data representing the traversal of the second signal through the physical structure at the second time, the third sequence of data representing the second signal adjusted based on the compensation statistic for the distortion of the second signal, relative to the first signal, that results from variation in the first ambient temperature and the second ambient temperature; and generating the compensated signal based on the third sequence of data, the compensated signal comprising the resolution fidelity that is maintained from the resolution fidelity of the second signal.

19. The one or more machine-readable hardware storage devices of claim 18, wherein the operations further comprise:

detecting, based on the scale factor and the scale invariant correlation coefficient, one or more areas of structural change in the physical structure.

* * * * *

UNITED STATES PATENT AND TRADEMARK OFFICE
CERTIFICATE OF CORRECTION

PATENT NO.         : 10,324,068 B2
APPLICATION NO.    : 13/945766
DATED              : June 18, 2019
INVENTOR(S)        : Joel B. Harley and Jose M. F. Moura It is certified that error appears in the above-identified patent and that said Letters Patent is hereby corrected as shown below:

In the Specification

Column 6, Line 63, delete "sinc" and insert -- sine --

Column 15, Line 63, delete "sinc" and insert -- sine --

Column 15, Line 64, delete "sinc" and insert -- sine --

Column 16, Line 1, delete "sinc" and insert -- sine --

Column 22, Line 12, delete "sinc" and insert -- sine --

In the Claims

Column 28, Line 65, Claim 8, delete "$S^{-1}\{.\}$ represents an inverse scale transform." and insert -- $S^{-1}\{.\}$ represents an inverse scale transform. --

Signed and Sealed this
Twentieth Day of August, 2019

Andrei Iancu
*Director of the United States Patent and Trademark Office*